(12) United States Patent
Xu et al.

(10) Patent No.: US 12,311,553 B2
(45) Date of Patent: May 27, 2025

(54) ROBOT SYSTEM AND CONTROL METHOD

(71) Applicant: BEIJING SURGERII ROBOTICS COMPANY LIMITED, Beijing (CN)

(72) Inventors: Kai Xu, Beijing (CN); Jiangran Zhao, Beijing (CN); Haozhe Yang, Beijing (CN)

(73) Assignee: BEIJING SURGERII ROBOTICS COMPANY LIMITED, Beiing (CN)

( * ) Notice: Subject to any disclaimer, the term of this patent is extended or adjusted under 35 U.S.C. 154(b) by 245 days.

(21) Appl. No.: 18/013,757

(22) PCT Filed: Jul. 29, 2021

(86) PCT No.: PCT/CN2021/109302
§ 371 (c)(1),
(2) Date: Dec. 29, 2022

(87) PCT Pub. No.: WO2022/037385
PCT Pub. Date: Feb. 24, 2022

(65) Prior Publication Data
US 2023/0294284 A1    Sep. 21, 2023

(30) Foreign Application Priority Data

Aug. 19, 2020 (CN) .......................... 202010837232.8
Aug. 19, 2020 (CN) .......................... 202010838021.6

(51) Int. Cl.
*B25J 9/16*     (2006.01)
*A61B 34/30*    (2016.01)
*B25J 9/00*     (2006.01)

(52) U.S. Cl.
CPC ............ *B25J 9/1664* (2013.01); *A61B 34/30* (2016.02); *B25J 9/0087* (2013.01); *A61B 2034/302* (2016.02)

(58) Field of Classification Search
CPC ...... B25J 9/1664; B25J 9/0087; B25J 9/1682; A61B 34/30; A61B 2034/302;
(Continued)

(56) References Cited

U.S. PATENT DOCUMENTS

2004/0199290 A1   10/2004   Stoddard et al.
2011/0190937 A1    8/2011   Ortmaier
(Continued)

FOREIGN PATENT DOCUMENTS

CN    104002296 A    8/2014
CN    105188590 A   12/2015
(Continued)

OTHER PUBLICATIONS

Supplementary European Search Report in related European Application No. 21857480 dated Jul. 30, 2024 (8 pages).
(Continued)

*Primary Examiner* — Kira Nguyen
(74) *Attorney, Agent, or Firm* — Bayes PLLC

(57) ABSTRACT

A control method for a robot system is provided. The robot system includes a plurality of motion arms, and the plurality of motion arms include a first motion arm and a second motion arm. The control method includes: determining a motion mode of ends of the first motion arm and the second motion arm of the robot system, where the motion mode includes synchronous motion of the ends of the first motion arm and the second motion arm; determining motion paths of the first motion arm and the second motion arm based on the motion mode and a relative end pose relationship between the first motion arm and the second motion arm; and controlling, based on the corresponding motion paths, the first motion arm and the second motion arm to move.

20 Claims, 10 Drawing Sheets

(58) Field of Classification Search
CPC .... A61B 2034/2059; A61B 2034/2061; A61B 2090/3612
USPC ......................................................... 700/254
See application file for complete search history.

(56) References Cited

U.S. PATENT DOCUMENTS

| | | | | |
|---|---|---|---|---|
| 2014/0163736 A1* | 6/2014 | Azizian | ................. | A61B 34/20 700/259 |
| 2017/0189126 A1* | 7/2017 | Weir | ...................... | A61B 34/25 |
| 2017/0189131 A1 | 7/2017 | Weir | | |
| 2017/0340396 A1 | 11/2017 | Romo et al. | | |
| 2019/0202066 A1* | 7/2019 | Maret | .................... | B25J 17/025 |
| 2019/0307519 A1* | 10/2019 | Popovic | ................. | A61B 34/32 |

FOREIGN PATENT DOCUMENTS

| | | |
|---|---|---|
| CN | 107116553 A | 9/2017 |
| CN | 107427327 A | 12/2017 |
| CN | 107427328 A | 12/2017 |
| CN | 108175510 A | 6/2018 |
| CN | 109091230 A | 12/2018 |
| CN | 109397244 A | 3/2019 |
| CN | 109591014 A | 4/2019 |
| CN | 109676610 A | 4/2019 |
| CN | 109699177 A | 4/2019 |
| CN | 110072483 A | 7/2019 |
| CN | 110464470 A | 11/2019 |
| CN | 110547874 A | 12/2019 |
| EP | 2467074 B1 | 1/2019 |
| JP | H10-296671 A | 11/1998 |
| JP | 2018500054 A | 1/2018 |
| KR | 20150023273 A | 3/2015 |
| KR | 20160008130 A | 1/2016 |
| WO | 2016054256 A1 | 4/2016 |

OTHER PUBLICATIONS

Office Action in related Canadian Application No. 3173684 dated Mar. 8, 2024 (4 pages).
Office Action in related Japanese Application No. 2022-580281 dated Dec. 26, 2023 (9 pages).
International Search Report and Written Opinion in related PCT Application No. PCT/CN2021/109302 dated Nov. 1, 2021 (10 pages).
Search Report in related Chinese Application No. 2021108664778 dated Feb. 19, 2025 (3 pages).
Search Report in related Chinese Application No. 2021108726011 dated Feb. 21, 2025 (2 pages).
Search Report in related Chinese Application No. 2021109032192 dated Feb. 26, 2025 (2 pages).
Search Report in related Korean Application No. 10-2022-7040611 dated Feb. 24, 2025 (6 pages).

* cited by examiner

ROBOT SYSTEM AND CONTROL METHOD

CROSS-REFERENCE TO RELATED APPLICATIONS

The present application is a national stage of International Application No. PCT/CN2021/109302, filed on Jul. 29, 2021, which claims priority to Chinese Patent Application No. 202010838021.6, filed on Aug. 19, 2020, and Chinese Patent Application No. 202010837232.8, filed on Aug. 19, 2020. The entire contents of each of the above-identified applications are expressly incorporated herein by reference.

TECHNICAL FIELD

The present disclosure relates to the field of robotics, and in particular, to a robot system and a control method.

BACKGROUND

Laparoscopy is a type of surgery that has been widely applied, and has advantages of small incision sizes and the like. In recent years, motion arms of surgical robots are used during surgeries to achieve higher stability and precision. During a surgery, a motion arm introduces a surgical instrument to a surgical site in a body (for example, the body of a human or an animal) through a trocar, to conduct the surgery.

At present, a surgical robot is mainly used for surgical procedures including preoperative positioning, intraoperative operation, and postoperative arrangement. Before a surgery, it is usually necessary that a surgical assistant (for example, an assistant surgeon or a nurse) adjusts a motion arm to a proper pose based on a type and pose of the surgery, connects the motion arm to a trocar in a fixed manner, and disposes a surgical instrument at an end of the motion arm, such that the surgical instrument is introduced into the body through the trocar. Motion of the motion arm may be adjusted manually by the surgical assistant at a farther end of the motion arm (that is, an end close to a patient), or may be controlled by the surgical assistant or surgeon with operations on a control apparatus at a nearer end of the motion arm (that is, an end close to a place where control is performed by the surgeon). However, the motion arm may have risks of instability and collisions due to a large size and heavy weight, especially in single-incision surgeries. As a result, it is complicated and time-consuming to adjust the motion arm. Similarly, such problems also exist in adjustment of the motion arm during and after a surgery.

SUMMARY

In some embodiments, the present disclosure provides a control method for a robot system, where the robot system includes a plurality of motion arms, the plurality of motion arms include a first motion arm and a second motion arm, and the control method includes: determining a motion mode of a first end of the first motion arm and a second end of the second motion arm of the robot system, where the motion mode includes synchronous motion of the first end of the first motion arm and the second end of the second motion arm; determining a first motion path of the first motion arm and a second motion path of the second motion arm based on the motion mode and a relative end pose relationship between the first end of the first motion arm and the second end of the second motion arm; and controlling, based on the first motion path and the second motion path, the first motion arm and the second motion arm to move, such that the first end of the first motion arm and the second end of the second motion arm move in the motion mode, and the relative end pose relationship remains unchanged during the motion.

In some embodiments, the present disclosure provides a robot system, including: a plurality of motion arms, where the plurality of motion arms include: a first motion arm; a second motion arm; and a control apparatus configured to: determine a motion mode of a first end of the first motion arm and a second end of the second motion arm of the robot system, where the motion mode includes synchronous motion of the first end of the first motion arm and the second end of the second motion arm; determine a first motion path of the first motion arm and a second motion path of the second motion arm based on the motion mode and a relative end pose relationship between the first end of the first motion arm and the second end of the second motion arm; and control, based on the first motion path and the second motion path, the first motion arm and the second motion arm to move, such that the first end of the first motion arm and the second end of the second motion arm move in the motion mode, and the relative end pose relationship remains unchanged during the motion.

In some embodiments, the present disclosure provides a computer-readable storage medium including one or more instructions, where the instructions are executed by a processor to perform a control method for a robot system; and the robot system includes a plurality of motion arms, the plurality of motion arms include a first motion arm and a second motion arm, and the control method includes: determining a motion mode of a first end of the first motion arm and a second end of the second motion arm of the robot system, where the motion mode includes synchronous motion of the first end of the first motion arm and the second end of the second motion arm; determining a first motion path of the first motion arm and a second motion path of the second motion arm based on the motion mode and a relative end pose relationship between the first end of the first motion arm and the second end of the second motion arm; and controlling, based on the first motion path and the second motion path, the first motion arm and the second motion arm to move, such that the first end of the first motion arm and the second end of the second motion arm move in the motion mode, and the relative end pose relationship remains unchanged during the motion.

BRIEF DESCRIPTION OF DRAWINGS

To clearly describe technical solutions in embodiments of the present disclosure, the accompanying drawings needed and used for descriptions in the embodiments of the present disclosure are briefly introduced below. The accompanying drawings in the following descriptions show merely some embodiments of the present disclosure, and those of ordinary skill in the art may still derive other embodiments from these accompanying drawings according to content of the embodiments of the accompanying drawings without creative efforts.

DETAILED DESCRIPTION

Figure 1:
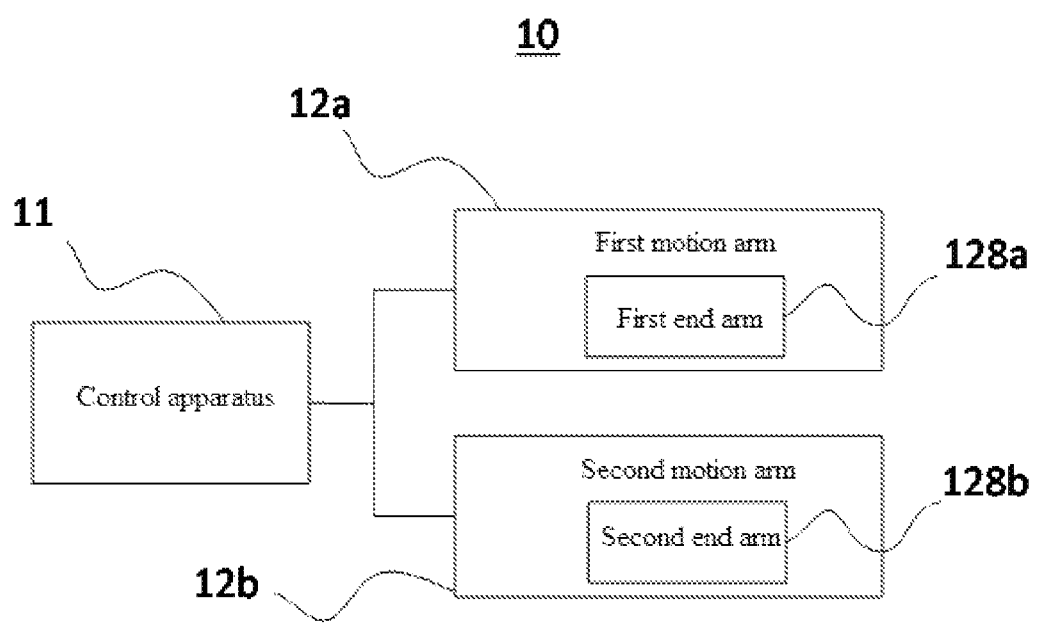
FIG. 1 is a block diagram of a structure of a robot system according to some embodiments of the present disclosure.

To make the resolved technical problems, used technical solutions, and achieved technical effects of the present disclosure more clearer, the technical solutions in embodiments of the present disclosure are further described in detail below with reference to the accompanying drawings. Apparently, the described embodiments are merely exemplary rather than all of the embodiments of the present disclosure.

In descriptions of the present disclosure, it should be noted that, direction or position relationships indicated by terms "central", "upper", "lower", "left", "right", "vertical", "horizontal", "inner", "outer", and the like are direction or position relationships based on the accompanying drawings, and are merely intended to facilitate the descriptions of the present disclosure and simplify the descriptions, rather than indicating or implying that a referred apparatus or element must have a particular direction or be constructed or operated in a particular direction. Therefore, these terms should not be interpreted as limiting the present disclosure. In addition, the terms "first" and "second" are for descriptive purposes only and should not be construed as indicating or implying relative importance. It should be noted that, in the descriptions of the present disclosure, unless expressly specified and limited otherwise, the terms "mounted", "connected to each other", "connected to", and "coupled" should be understood in a broad sense. For example, "connection" may be a fixed connection, a detachable connection, a mechanical connection, or an electrical connection; or may be a direct connection or an indirect connection by means of an intermediate medium; or may be an internal communication between two elements. For those of ordinary skill in the art, specific meanings of the foregoing terms in the present disclosure may be understood based on specific situations. In the present disclosure, in a surgical robot system, an end closer to a user (for example, a surgeon) is defined as a nearer end, a nearer part, a rear end, or a rear part, and an end closer to a surgical patient is defined as a farther end, a farther part, a front end, or a front part. Those skilled in the art may understand that the embodiments of the present disclosure may be applied to medical devices or surgical robots, or may be applied to other non-medical apparatuses.

In the present disclosure, the term "position" refers to a location of an object or a part of the object in three-dimensional space (for example, changes in Cartesian X, Y, and Z coordinates may be used to describe three translational degrees of freedom, for example, three translational degrees of freedom along the Cartesian X-axis, Y-axis, and Z-axis). In the present disclosure, the term "posture" refers to a setting of rotation of an object or a part of the object (for example, three rotational degrees of freedom may be described by roll, pitch, and yaw). In the present disclosure, the term "pose" refers to a combination of a position and an posture of an object or a part of the object and may be described by, for example, six parameters of the six degrees of freedom mentioned above. In the present disclosure, a pose of a motion arm or a part of the motion arm refers to a pose indicated by a coordinate system defined by the motion arm or the part of the motion arm relative to a coordinate system defined by a support or a base of the motion arm or a world coordinate system. In the present disclosure, a position of a motion arm or a part of the motion arm may be represented by a set of joint values (for example, a one-dimensional matrix of these joint values) of a plurality of joints of the motion arm. In the present disclosure, a joint value of a joint may include an angle by which the corresponding joint rotates about the corresponding joint axis or a distance by which the corresponding joint moves relative to an initial position of the joint. In the present disclosure, a motion path of a motion arm refers to a path along which the motion arm moves from one position or posture to another position or posture.

FIG. 1 is a block diagram of a structure of a robot system 10 according to some embodiments of the present disclosure. As shown in FIG. 1, the robot system 10 may include a control apparatus 11 and a plurality of motion arms connected to the control apparatus 11. In some embodiments, as shown in FIG. 1, the plurality of motion arms may include a first motion arm 12a and a second motion arm 12b. The control apparatus 11 may be configured to control the first motion arm 12a and the second motion arm 12b. For example, the control apparatus 11 may adjust motion, poses, mutual coordination, and the like of the first motion arm 12a and the second motion arm 12b. In some embodiments, the first motion arm 12a and the second motion arm 12b may respectively include a first end arm 128a and a second end arm 128b at ends or farther ends. The control apparatus 11 may control the first motion arm 12a or the second motion arm 12b to move, such that the first end arm 128a or the second end arm 128b moves to an expected position or posture.

For brevity of description in the present disclosure, FIG. 1 and subsequent drawings show an example in which the robot system 10 includes two motion arms. However, those skilled in the art should understand that the robot system 10 may alternatively include three, four, or more motion arms. The robot system 10 may include a surgical robot system, for example, a robot system for endoscopic surgeries. It should be understood that the robot system 10 may alternatively include a dedicated or general-purpose robot system applied in other fields (such as manufacturing and machinery).

Figure 2:
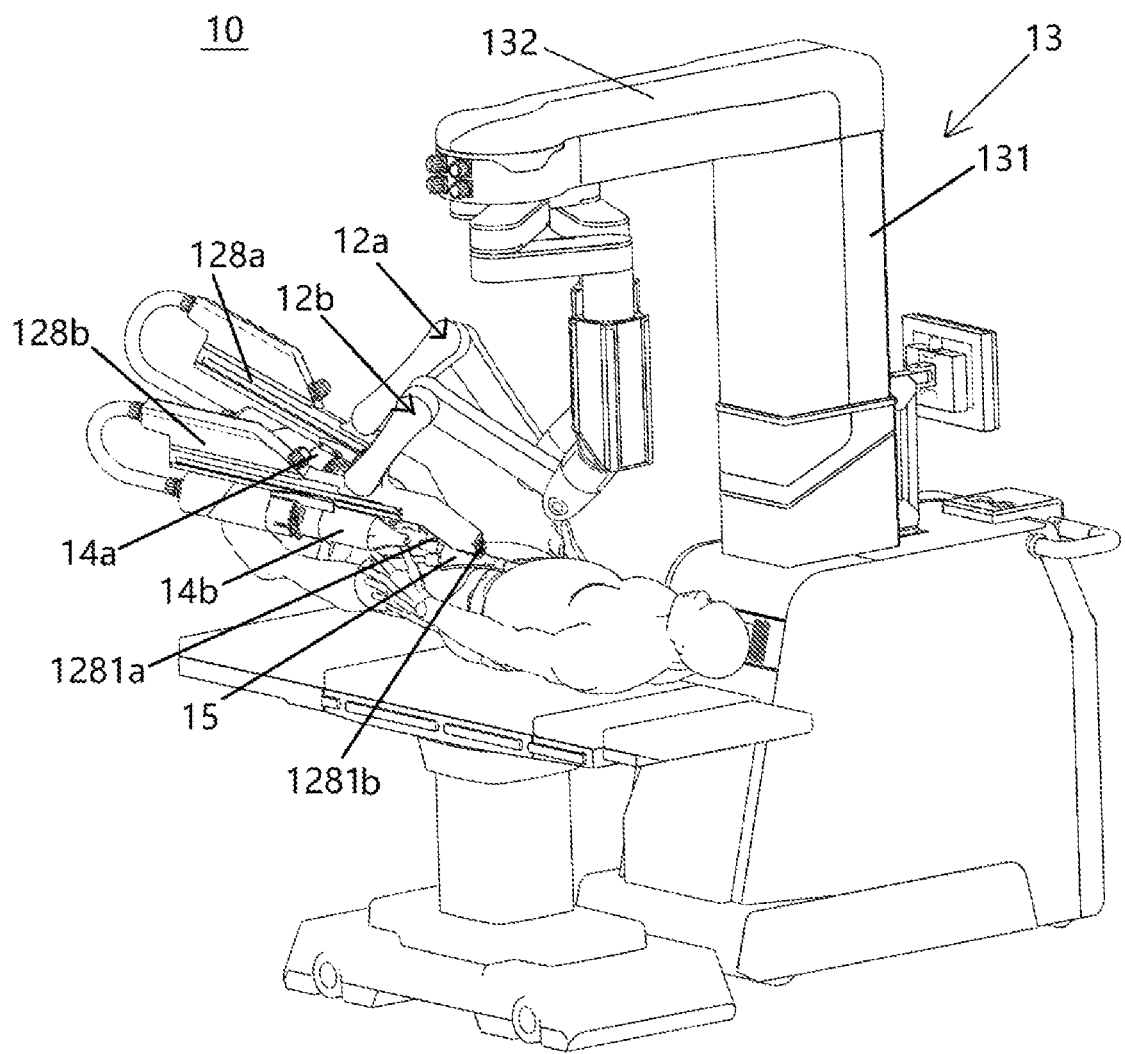
FIG. 2 is a schematic diagram of a three-dimensional structure of a robot system according to some embodiments of the present disclosure.

FIG. 2 is a schematic diagram of a three-dimensional structure of the robot system 10 according to some embodiments of the present disclosure. As shown in FIG. 2, the robot system 10 is a surgical robot system and may include a patient-side cart 13 and a first motion arm 12a and a second motion arm 12b disposed on the patient-side cart 13. In some embodiments, the patient-side cart 13 may include a base 131 and a beam 132. In some embodiments, the first motion arm 12a and the second motion arm 12b may be disposed on the beam 132 in a movable manner. It should be understood that a plurality of motion arms of the robot system 10 may alternatively be disposed on a plurality of patient-side carts. For example, each motion arm is disposed on a corresponding patient-side cart. Alternatively, one motion arm is disposed on one patient-side cart, and a plurality of other motion arms are disposed on another patient-side cart. These embodiments still fall within the protection scope of the present disclosure.

In some embodiments, each motion arm (for example, the first motion arm 12a and the second motion arm 12b) of the robot system 10 may include a plurality of connecting rods and a plurality of joints. In some embodiments, each joint of each motion arm may include a motor used for driving the corresponding joint to move, to further drive a corresponding connecting rod to rotate.

Figure 3:
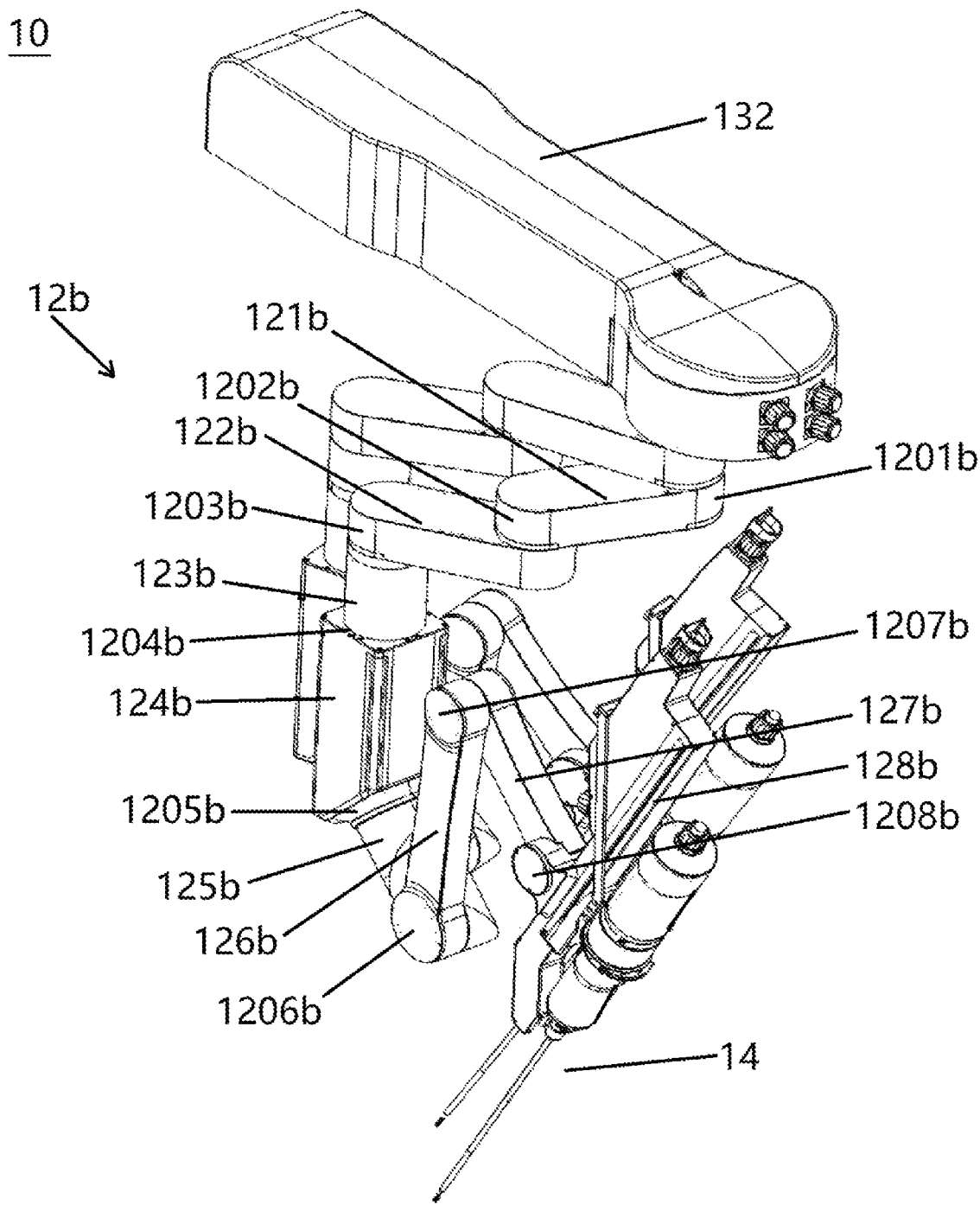
FIG. 3 is a schematic structural diagram of a motion arm of a robot system according to some embodiments of the present disclosure.

FIG. 3 is a schematic structural diagram of a motion arm of the robot system 10 according to some embodiments of the present disclosure. As shown in FIG. 3, a second motion arm 12b (or a first motion arm 12a) may include joints 1201b to 1208b and connecting rods 121b to 128b. A nearer end (in the present disclosure, an end closer to the beam 132 is defined as a nearer end of a motion arm) of the connecting rod 121b is connected to the beam 132. The connecting rods 121b to 127b are connected successively. The joint 1201b may be located at a nearer-end connection of the beam 132 and the connecting rod 121b, the joint 1202b may be located at a connection of the connecting rod 121b and the second connecting rod 122b, the joint 1203b may be located at a connection of the connecting rod 122b and the connecting rod 123b, the joint 1204b may be located at a connection of the connecting rod 123b and the connecting rod 124b, the joint 1205b may be located at a connection of the connecting rod 124b and the connecting rod 125b, the joint 1206b may be located at a connection of the connecting rod 125b and the connecting rod 126b, the joint 1207b may be located at a connection of the connecting rod 126b and the connecting rod 127b, and the joint 1208b may be located at a connection of the connecting rod 127b and the connecting rod 128b. As the connecting rod at the farthest end of the second motion arm 12b, the connecting rod 128b is used as a second end arm 128b of the second motion arm 12b. Determination and representation of a position and an posture of the end arm depend on all the foregoing joints. It should be understood that the connecting rods 126b, 127b, and 128b together form a remote center of motion mechanism (RCM mechanism) of the second motion arm 12b.

In some embodiments, the robot system 10 may include one or more surgical instruments. As shown in FIG. 3, a surgical instrument 14a may be mounted on a first end arm 128a of the first motion arm 12a, and a surgical instrument 14b may be mounted on the second end arm 128b of the second motion arm 12b. It should be understood that the surgical instrument 14a and the surgical instrument 14b may include, but are not limited to, surgical forceps, an electric scalpel, or an image capturing device for illuminated imaging (for example, an endoscopic tool). Parts of the surgical instrument 14a and the surgical instrument 14b (such as an arm and an end instrument at a farther end of the arm) may enter a body part of a human or an animal to conduct medical operations such as a surgery.

In some embodiments, as shown in FIG. 2, the robot system 10 may further include an auxiliary connection apparatus 15, for example, a cannula sheath. The auxiliary connection apparatus 15 may be mounted on the body of a human or an animal (for example, in an incision or an opening), with one part perhaps located at a body part, where a surgery is required, of the human or the animal and the other part connected to the motion arm (for example, the first end arm 128a of the first motion arm 12a and the second end arm 128b of the second motion arm 12b) in a detachable manner, thereby serving the surgery in a better way.

Figure 4:
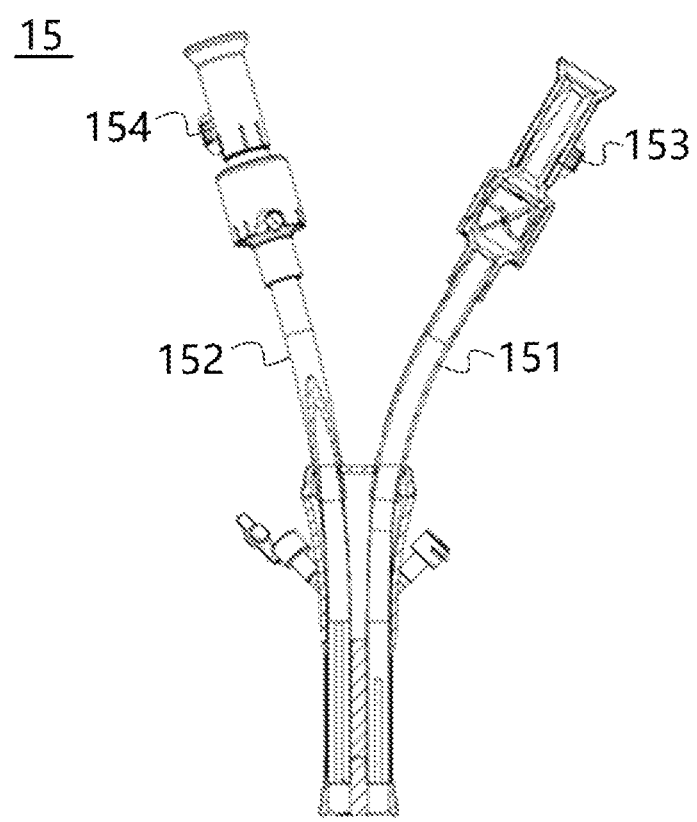
FIG. 4 is a partial sectional view of an auxiliary connection apparatus according to some embodiments of the present disclosure.

FIG. 4 is a partial sectional view of the auxiliary connection apparatus 15 according to some embodiments of the present disclosure. In some embodiments, as shown in FIG. 4, the auxiliary connection apparatus 15 may include a cannula 151 and a cannula 152. In some embodiments, the auxiliary connection apparatus 15 may further include at least two connection portions (such as a connection portion 153 and a connection portion 154). A connection portion may include, but is not limited to, forceps, a clamping structure, a bonding structure, a plug-in structure, and a pull-in structure. The connection portions 153 and 154 may be respectively disposed on the cannulas 151 and 152 in a fixed manner.

In some embodiments, connectors (such as connectors 1281a and 1281b shown in FIG. 2) co-used with the connection portions (such as the connection portions 153 and 154) may be disposed on each motion arm (for example, a first motion arm 12a and a second motion arm 12b). The auxiliary connection apparatus 15 may be connected to the connectors 1281a and 1281b on the first motion arm 12a and the second motion arm 12b in a fixed and detachable manner through the connection portions 153 and 154 respectively. In some embodiments, as shown in FIG. 2, the connectors 1281a and 1281b may be disposed, in a fixed manner, on the first end arm 128a and the second end arm 128b respectively. The connectors 1281a and 1281b are connected to the connection portion 153 and the connection portion 154 respectively, such that the auxiliary connection apparatus 15 is connected to the first motion arm 12a and the second motion arm 12b in a fixed and detachable manner.

It should be understood that spatial positions described by Cartesian coordinates and postures described by rotating coordinates of the first end arm 128a, the second end arm 128b, and the connectors 1281a and 1281b may be represented by coordinate vectors. In some embodiments, a type of a current surgery or configuration of the auxiliary connection apparatus may be used as a basis. For example, the configuration of the auxiliary connection apparatus may be determined based on the type of the current surgery. Shapes of and a relative position relationship between a plurality of cannulas of the auxiliary connection apparatus are determined based on the configuration of the auxiliary connection apparatus, to determine relative end poses of a plurality of motion arms. It should be understood that an end of a motion arm may include an end arm of the motion arm, a remote center of motion mechanism (RCM mechanism) of the motion arm, or a part, for being connected to the auxiliary connection apparatus, of the motion arm. A pose of the end of the motion arm may include a pose of the end arm of the motion arm, a pose of the remote center of motion mechanism (RCM mechanism) of the motion arm, or a pose of the part, for being connected to the auxiliary connection apparatus, of the motion arm.

For example, a relative end pose relationship between the first motion arm 12a and the second motion arm 12b may be determined based on shapes of and a relative position relationship between the cannulas 151 and 152. The relative end pose relationship between the first motion arm 12a and second motion arm 12b may indicate a relative position relationship and a relative posture relationship between an end of the first motion arm 12a and an end of the second motion arm 12b in the world space coordinate system. It should be understood that the relative end pose relationship may include, for example, a relative pose relationship between the first end arm 128a of the first motion arm 12a and the second end arm 128b of the second motion arm 12b. Alternatively, the relative end pose relationship may include a relative pose relationship between the surgical instruments 14a and 14b that are mounted on the first end arm 128a and the second end arm 128b. Alternatively, the relative end pose relationship may include a relative pose relationship between the connectors 1281a and 1281b that are disposed on the first end arm 128a and the second end arm 128b in a fixed manner. In some embodiments, the relative end pose relationship may be stored in an associated relative pose model, and may be used for calculating target poses of the ends of the first motion arm 12a and the second motion arm 12b. Because the connectors 1281a and 1281b are fixed onto the first end arm 128a and the second end arm 128b respectively, when the first end arm 128a and the second end arm 128b satisfy the relative end pose relationship, the connectors 1281a and 1281b may be connected to the connection portions 153 and 154 respectively.

It should be understood that, when the first motion arm 12a moves to a target pose, a target pose of the surgical instrument 14a mounted at the end of the first motion arm 12a in the world coordinate system may be determined, and when the second motion arm 12b moves to a target pose, a target pose of the surgical instrument 14b mounted at the end of the second motion arm 12b in the world coordinate system may be determined. An posture of a motion arm or a part of the motion arm may be implemented by using joints. For example, in some embodiments, a target spatial position of a fixed part (for example, the first end arm 128a and the second end arm 128b, the connectors 1281a and 1281b disposed on the first motion arm 12a and the second motion arm 12b in a fixed manner, or the surgical instruments 14a and 14b mounted on the first motion arm 12a and the second motion arm 12b) on each motion arm may be implemented by using some joints in a plurality of joints of the corresponding motion arm. A target spatial posture of a fixed part of each motion arm may be implemented by using other joints in a plurality of joints of the corresponding motion arm. In some embodiments, the plurality of joints at an end (for example, the first end arm 128a and the second end arm 128b) of the motion arm for implementing the target spatial posture are closer to a farther end of the motion arm than the plurality of joints of the motion arm for implementing the target spatial position. It should be understood that the plurality of joints for implementing the target spatial posture and the target spatial position of the end of the motion arm may alternatively be disposed in another manner, and may be specifically disposed according to usage requirements.

In some embodiments, after the surgical instruments are mounted onto end arms, the surgical instruments 14a and 14b respectively pass through the cannulas 151 and 152 of the auxiliary connection apparatus 15, respectively come out of the cannulas 151 and 152 smoothly at predetermined angles, and enter a human body along the cannulas 151 and 152 to reach a corresponding pose for a surgery. In some embodiments, the cannulas 151 and 152 of the auxiliary connection apparatus 15 may be flexible, and parts of the auxiliary connection apparatus 15 through which the surgical instruments 14a and 14b extend to pass are also flexible, such that when the relative end pose relationship between the first end arm 128a and the second end arm 128b is roughly satisfied, the connection portions 153 and 154 on the auxiliary connection apparatus 15 may be connected to the connectors 1281a and 1281b on each motion arm; and the flexible parts of the auxiliary connection apparatus 15 may ensure that each surgical instrument can still enter a surgical region through a cannula when there is a specific error in a pose of an end arm.

It should be understood that the auxiliary connection apparatus 15 shown in FIG. 4 is merely an example. In some embodiments, the robot system 10 may include three, four, or more motion arms. The auxiliary connection apparatus 15 may include three, four, or more cannulas, and each cannula includes a corresponding connection portion used to connect the cannula to each corresponding motion arm and constrain a relative end pose relationship between the plurality of end arms.

Figure 5:
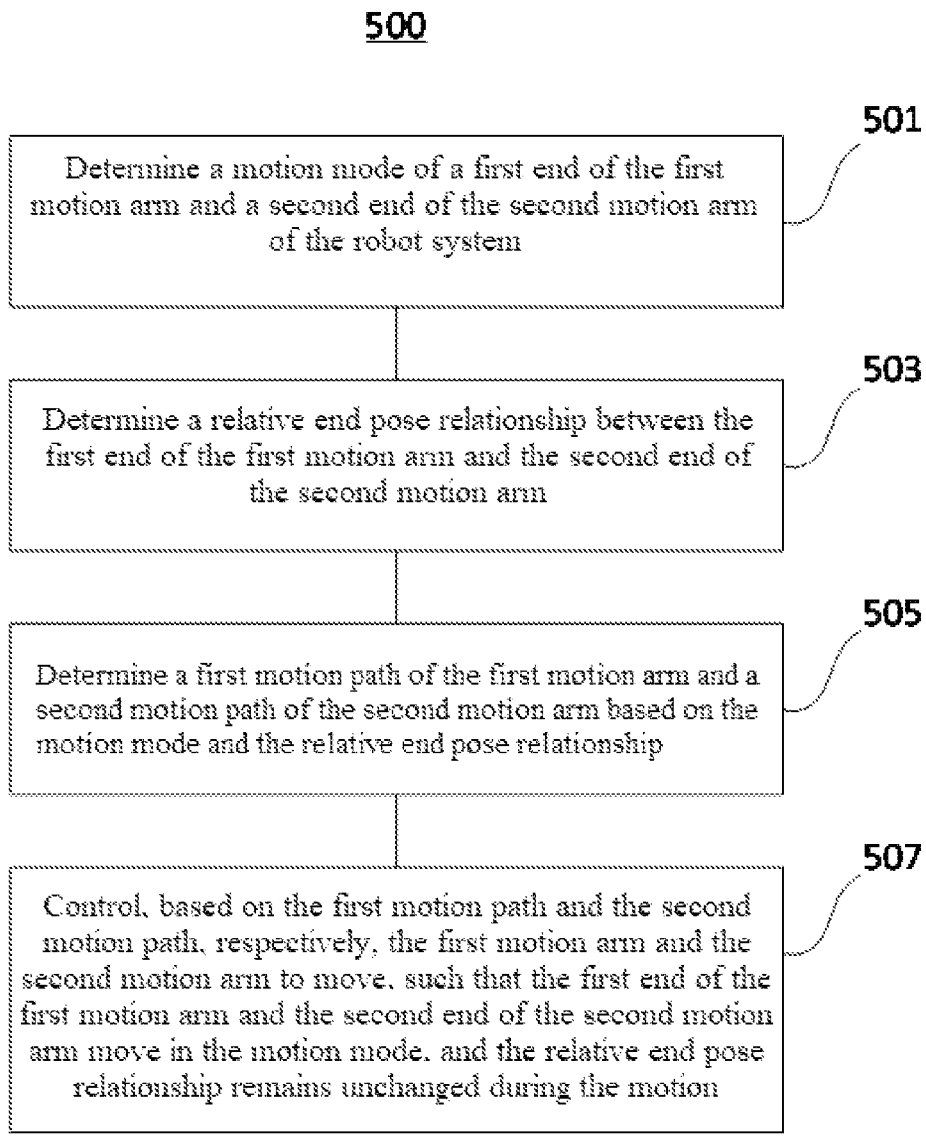
FIG. 5 is a flowchart of a control method for a robot system according to some embodiments of the present disclosure.
Figure 6:
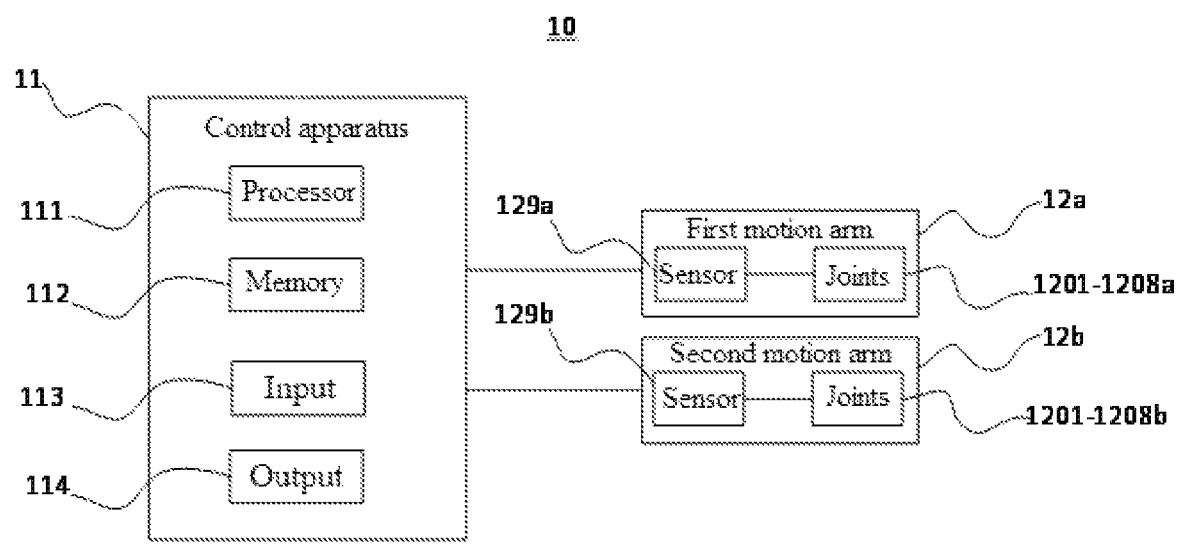
FIG. 6 is another block diagram of a structure of a robot system according to some embodiments of the present disclosure.

The present disclosure provides a control method for a robot system. FIG. 5 is a flowchart of a control method 500 for a robot system (for example, the robot system 10) according to some embodiments of the present disclosure. FIG. 6 is another simplified block diagram of the robot system 10 according to some embodiments of the present disclosure. As shown in FIG. 5 and FIG. 6, the method 500 may be performed by a control apparatus (for example, a control apparatus 11) of the robot system 10. The control apparatus 11 may be mounted on a computing device. The method 500 may be implemented by software, firmware, and/or hardware.

As shown in FIG. 5, in step 501, a motion mode of a first end of a first motion arm and a second end of a second motion arm of the robot system is determined. In some embodiments, the motion mode may include synchronous motion of an end (for example, a first end arm 128a) of a first motion arm 12a and an end (for example, a second end arm 128b) of a second motion arm 12b. For example, the synchronous motion may include, but is not limited to, synchronous translation, synchronous rotation, or a combination of synchronous translation and synchronous rotation. It should be understood that synchronous rotation of an end may include a pitch or horizontal rotation about a predetermined point. In some embodiments, the predetermined point may be a connection point of an auxiliary connection apparatus 15 and an incision, or the predetermined point may include a point on an extension line of an end of a motion arm, for example, a remote center of motion (RCM) point.

In some embodiments, the control apparatus 11 may determine a motion mode of the ends of the first motion arm 12a and the second motion arm 12b according to an operating command. In some embodiments, the control apparatus 11 may include an input apparatus 113. The input apparatus 113 may be configured to: receive an operating command from a user; or receive an operating instruction from a user, so that the control apparatus 11 can obtain a specific operating command based on the operating instruction. For example, in a case in which the motion mode is the synchronous translation, the operating command may be a command that the first end arm 128a of the first motion arm 12a and the second end arm 128b of the second motion arm 12b translate together as a whole. In a case in which the motion mode is the synchronous rotation, the operating command may be a command that the first end arm 128a of the first motion arm 12a and the second end arm 128b of the second motion arm 12b rotate about a predetermined point or straight line together as a whole. For example, the first end arm 128a of the first motion arm 12a and the second end arm 128b of the second motion arm 12b rotate up and down about the predetermined point or rotate about a longitudinal axis together as a whole. In a case in which the motion mode is a combination of the synchronous translation and the synchronous rotation, the operating command may be a command that the first end arm 128a of the first motion arm 12a and the second end arm 128b of the second motion arm 12b translate and rotate together as a whole.

In step 503, optionally, the method 500 may include: determining a relative end pose relationship between the first end of the first motion arm and the second end of the second motion arm. In some embodiments, the relative end pose relationship between the end (for example, the first end arm 128a) of the first motion arm 12a and the end (for example, the second end arm 128b) of the second motion arm 12b may be determined based on a type of a current surgery or configuration of an auxiliary connection apparatus (for example, the auxiliary connection apparatus 15). In some embodiments, the relative end pose relationship between the first end of the first motion arm and the second end of the second motion arm may be predetermined or already known.

In some embodiments, the type of the current surgery may be a type of a surgery that is currently required. For example, the surgery type may include, but is not limited to, a general surgery, a thoracic surgery, a urological surgery, and a gynecological surgery. In some embodiments, the auxiliary connection apparatus may include a cannula sheath, where configuration of the cannula sheath may include, for example, specifications and models of cannula sheaths for different types of surgeries (the specifications and the models may include, but are not limited to, for example, lengths, radial dimensions, inner diameters, the number of cannulas of the cannula sheaths, and a relative position relationship between the plurality of disposed cannulas). Each of the plurality of cannula sheaths is associated with a relative pose relationship of at least one motion arm. There may be different relative pose relationships between cannula sheaths with different configurations and each motion arm. In some embodiments, the input apparatus 113 may be used for receiving setting information from a user (for example, setting information about the type of the current surgery, the configuration of the auxiliary connection apparatus, and the relative pose model).

In some embodiments, the relative end pose relationship may include a relative position relationship and a relative posture relationship between the first end arm 128a of the first motion arm 12a and the second end arm 128b of the second motion arm 12b. In some embodiments, surgical instruments 14a and 14b may be mounted on the first end arm 128a and the second end arm 128b, where the relative end pose relationship may include a relative position relationship and a relative posture relationship between the surgical instruments 14a and 14b. It should be understood that a relative pose relationship between the surgical instruments 14a and 14b may be determined based on the relative pose relationship between the first end arm 128a and the second end arm 128b. In some embodiments, the relative end pose relationship may further include a relative position relationship and a relative posture relationship between connectors 1281a and 1281b. The connectors 1281a and 1281b are disposed, in a fixed manner, on the first end arm 128a and the second end arm 128b respectively. In this way, the relative pose relationship between the surgical instruments 14a and 14b may alternatively be determined based on a relative pose relationship between the connectors 1281a and 1281b. It should be understood that the relative pose relationship between the surgical instruments, the relative pose relationship between the end arms, and the relative pose relationship between the connectors may be transformed into one another.

In some embodiments, the relative end pose relationship between the end of the first motion arm 12a and the end of the second motion arm 12b may alternatively be determined based on a current pose of the end of the first motion arm 12a and a current pose of the end of the second motion arm 12b. For example, during a surgery, the relative end pose relationship may be determined based on a current pose of the end arm 128a of the first motion arm 12a and a current pose of the end arm 128b of the second motion arm 12b.

In some embodiments, as shown in FIG. 6, the control apparatus 11 may be communicatively connected to various motion arms (such as the first motion arm 12a and the second motion arm 12b). In some embodiments, as shown in FIG. 6, the first motion arm 12a may further include one or more sensors 129a. Motors of joints 1201 to 1208a may be coupled to a plurality of sensors 129a respectively. The second motion arm 12b may further include one or more sensors 129b. Motors of joints 1201 to 1208b may be coupled to a plurality of sensors 129b respectively. FIG. 6 exemplarily shows a sensor. It should be understood that the illustrated sensors 129a and 129b may represent a plurality of sensors. The sensors 129a and 129b may include, but are not limited to, for example, an encoder or a potentiometer. The sensors may be used for obtaining data of a plurality of joints of the motion arms, to measure a joint value of a corresponding joint. In some embodiments, the sensors may include a fiber sensor extendedly disposed on the motion arms used for obtaining a pose of a motion arm.

In some embodiments, as shown in FIG. 6, the control apparatus 11 may include one or more processors 111 and memories 112. The processor 111 may be communicatively connected to the plurality of sensors 129a of the first motion arm 12a, to obtain current joint values of the joints 1201 to 1208a of the first motion arm 12a by using the plurality of sensors 129a. The processor 111 may be communicatively connected to the plurality of sensors 129b of the second motion arm 12b, to obtain current joint values of the joints 1201 to 1208b of the second motion arm 12b by using the plurality of sensors 129b.

In some embodiments, the processor 111 may calculate the current joint values of the joints based on forward kinematic models of the first motion arm 12a and the second motion arm 12b, to obtain current poses of the first motion arm 12a and the second motion arm 12b (for example, the ends of the first motion arm and the second motion arm). It should be understood that a current pose may include a current posture and a current position, and the current pose may be a position and an posture at any moment. The forward kinematic model of the first motion arm 12a may be preset and stored in the memory 112. According to a forward kinematic model of a motion arm, a pose of the motion arm at any position or a pose of any part of the motion arm (for example, poses of the first end arm 128a and the second end arm 128b, of the connectors 1281a and 1281b disposed on the first motion arm 12a and the second motion arm 12b in a fixed manner, or of the surgical instruments 14a and 14b mounted on the first motion arm 12a and the second motion arm 12b) may be obtained based on all known joint variables (such as the joint values) of the motion arm.

In step 505, a first motion path of the first motion arm and a second motion path of the second motion arm are determined based on the motion mode and the relative end pose relationship. It should be understood that, the motion path of the first motion arm 12a may refer to a path along which the first motion arm 12a moves from one pose to another pose, and may be represented by joint value changes (such as continuous changes of joint values or one or more transient joint values) of a plurality of joints (for example, the joints 1201 to 1208a). The motion path of the second motion arm 12b may refer to a path along which the second motion arm 12b moves from one position to another position, and may be represented by joint value changes of a plurality of joints (for example, the joints 1201 to 1208b).

In step 507, the first motion arm and the second motion arm are controlled, based on the first motion path and the second motion path respectively, to move, such that the end of the first motion arm and the end of the second motion arm move in the motion mode, and the relative end pose relationship remains unchanged during the motion.

In some embodiments, in the method 500, whether there is an interference relationship between the first motion arm 12a and the second motion arm 12b may further be determined based on the first motion path of the first motion arm 12a and the second motion path of the second motion arm 12b. Step 507 is performed in response to determination that there is no interference relationship between the first motion arm 12a and the second motion arm 12b. Alternatively, the first motion arm 12a and the second motion arm 12b are controlled to stop moving or alarm information is sent in response to determination that there is an interference relationship between the first motion arm 12a and the second motion arm 12b.

In some embodiments, the method 500 may include: receiving an operating command. In some embodiments, the operating command includes, for example, moving the first motion arm 12a and the second motion arm 12b a specific distance or rotating the first motion arm 12a and the second motion arm 12b a specific angle together as a whole.

In some embodiments, when steps 501 to 507 are performed, at least one of surgical instruments (for example, the surgical instruments 14a and 14b) may be disposed at an end of a corresponding motion arm (for example, the first end arm 128a of the first motion arm or the second end arm 128b of the second motion arm).

Figure 7:
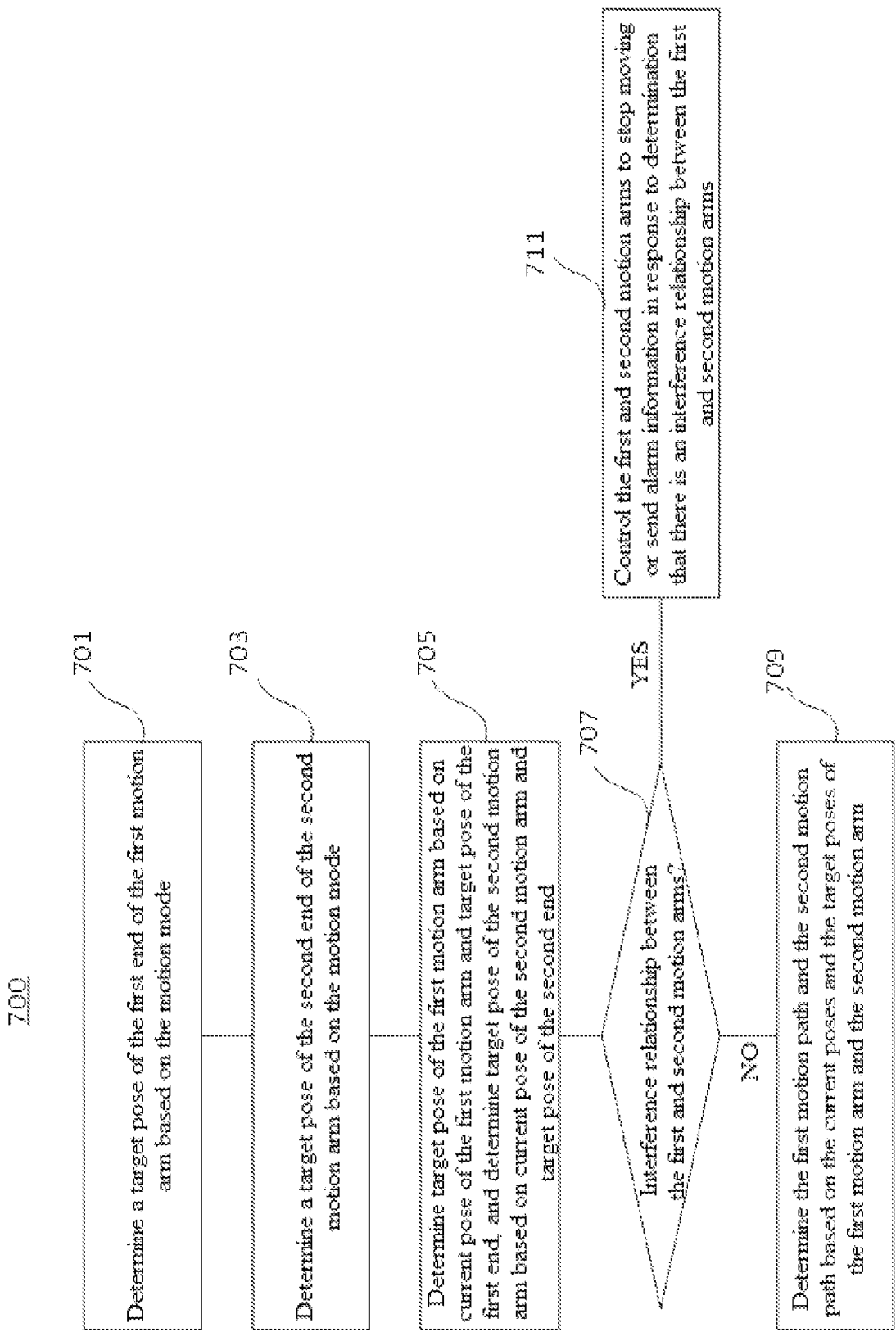
FIG. 7 is a flowchart of a method for determining a motion path of a motion arm according to some embodiments of the present disclosure.

FIG. 7 is a flowchart of a method 700 for determining a motion path of a motion arm according to some embodiments of the present disclosure. In some embodiments, the method 700 may be used to implement step 505 of determining a first motion path of the first motion arm and a second motion path of the second motion arm based on the motion mode and the relative end pose relationship, as shown in FIG. 5. The method 700 may be performed by a control apparatus (for example, a control apparatus 11) of a robot system 10. The control apparatus 11 may be mounted on a computing device. The method 700 may be implemented by software, firmware, and/or hardware.

In step 701, a target pose of the first end of the first motion arm is determined based on the motion mode. In some embodiments, the target pose of the first end may be determined based on an operating command received from a user. The operating command may include a target pose, a mode and range of motion, and the like. In some embodiments, a current pose of an end (for example, the first end arm 128a) of the first motion arm 12a may be obtained by solving the forward kinematic model of the first motion arm 12 based on the current joint values of the joints of the first motion arm 12a. The target pose of the first end of the first motion arm 12a may be determined based on a current pose of the end of the first motion arm 12a and the operating command from the user. For example, the target pose may be determined based on the current pose of the first end and the motion mode (for example, synchronous leftward movement or rotation) and range (for example, a moving distance or a rotation angle) of the first motion arm.

In some embodiments, the target pose of the first end of the first motion arm 12a may include one of the following: a target position and a target posture of the first end arm 128a of the first motion arm 12a, a target position and a target posture of a remote center of motion mechanism (RCM mechanism) of the first motion arm 12a, and a target position and a target posture of an end (for example, a connector 1281a), for being connected to an auxiliary connection apparatus 15, of the first motion arm 12a.

In step 703, a target pose of the second end of the second motion arm is determined based on the motion mode. In some embodiments, the target pose of the second end of the second motion arm may be determined based on the synchronous motion mode, the target pose of the first end, and the relative end pose relationship. In some embodiments, the target pose of the end of the second motion arm 12b may include one of the following: a target position and a target posture of the second end arm 128b of the second motion arm 12b, a target position and a target posture of a remote center of motion mechanism (RCM mechanism) of the second motion arm 12a, and a target position and a target posture of an end (for example, a connector 1281b), for being connected to the auxiliary connection apparatus 15, of the second motion arm 12b. It should be understood that, the target pose of the end of the second motion arm 12b may be determined based on the target pose of the end of the first motion arm 12a and the relative end pose relationship. In some embodiments, when surgical instruments 14a and 14b are disposed at the ends of the first motion arm 12a and the second motion arm 12b, target poses of the surgical instruments 14a and 14b may be determined based on the target poses of the ends of the first motion arm 12a and the second motion arm 12b.

In some embodiments, the method 700 may further include step 705. In step 705, a target pose of the first motion arm is determined based on a current pose of the first motion arm and the target pose of the first end, and a target pose of the second motion arm is determined based on a current pose of the second motion arm and the target pose of the second end. In some embodiments, the current joint values of the joints of the first motion arm 12a may be obtained by using a sensor (for example, a sensor 129a) mounted at each joint of the first motion arm 12a, and may be used for solving the forward kinematic model of the first motion arm 12a, to obtain the current pose of the first motion arm 12a. The current joint values of the joints of the second motion arm 12b may be obtained by using a sensor (for example, a sensor 129b) mounted at each joint of the second motion arm 12b, and may be used for solving the forward kinematic model of the second motion arm 12b, to obtain the current pose of the second motion arm 12b. It should be understood that a pose of a motion arm may be represented by a set of joint values of a plurality of joints of the motion arm. In some embodiments, a target pose of the motion arm may be determined based on a current pose of the motion arm and a target pose of an end according to the method shown in FIG. 8.

In step 709, the first motion path and the second motion path are determined based on the current poses and the target poses of the first motion arm and the second motion arm. In some embodiments, the first motion path of the first motion arm 12a and the second motion path of the second motion arm 12b may be determined based on an interpolation method, where a motion path may include at least one motion cycle. In some embodiments, a motion path of the motion arm from an initial pose to the target pose may be planned according to the method shown in FIG. 9.

In some embodiments, the method 700 may further include step 707. In step 707, whether there is an interference relationship between the first motion arm and the second motion arm is determined. It should be understood that the interference relationship may include a collision between the first motion arm 12a and the second motion arm 12b. Step 709 is performed in response to determination that there is no interference relationship between the first motion arm 12a and the second motion arm 12b.

In some embodiments, the method 700 may further include step 711. In step 711, the first motion arm and the second motion arm are controlled to stop moving or alarm information is sent in response to determination that there is an interference relationship between the first motion arm and the second motion arm.

In some embodiments, whether there is an interference relationship between the first motion arm 12a and the second motion arm 12b may be determined based on a constraint relationship. That there is no interference relationship between the first motion arm 12a and the second motion arm 12b is determined based on the constraint relationship that is satisfied. That there is an interference relationship between the first motion arm 12a and the second motion arm 12b is determined based on the constraint relationship that is not satisfied. It should be understood that the constraint relationship may be limited by using an interference model.

In some embodiments, the constraint relationship may include at least one of the following relationships: a relative position order relationship between the first motion arm 12a and the second motion arm 21b conforms to a predetermined relative position order relationship, a distance between a predetermined point associated with the first motion arm 12a and a predetermined point associated with the second motion arm 12b is greater than a predetermined safety distance, a minimum distance between a preset line segment associated with the first motion arm 12a and a preset line segment associated with the second motion arm 12b is greater than a predetermined line segment safety distance, or a difference between a joint value of one or more joints of the first motion arm 12a and a joint value of a corresponding joint of the second motion arm 12b is greater than a predetermined safety value.

In some embodiments, the predetermined relative position order relationship may include, but is not limited to that a plurality of motion arms are arranged in clockwise order or counterclockwise order. A relative position order relationship between the plurality of motion arms may be represented by a relative position order of joints or connecting rods of the motion arms. For example, when a relative position order of an ending position of one or more joints (for example, a joint 1202a and/or a joint 1203a), close to the beam 132, of the first motion arm 12a in each motion cycle and an ending position of one or more joints (for example, a joint 1202b and/or a joint 1203b), close to the beam 132, of an adjacent motion arm (for example, the second motion arm 12b) in each motion cycle conforms to a clockwise order or a counterclockwise order, that the first motion arm 12a and the second motion arm 12b satisfy a constraint of a relative position order relationship may be determined. Otherwise, that the first motion arm 12a and the second motion arm 12b do not satisfy a predetermined relative position relationship may be determined, and there may be an interference relationship between the first motion arm 12a and the second motion arm 12b. In some embodiments, whether the relative position order relationship between the first motion arm 12a and the second motion arm 12b conforms to the predetermined relative position order relationship may alternatively be determined by determining whether a relative position order between an end of one or more connecting rods (for example, a connecting rod 121a and/or a connecting rod 122a) of the first motion arm 12a and an end of a corresponding connecting rod (for example, a connecting rod 121b and/or a connecting rod 122b) of the second motion arm 12b conforms to the predetermined relative position order relationship (for example, a clockwise order or a counterclockwise order).

In some embodiments, the relative position order relationship between the plurality of motion arms may alternatively be represented by motion angles of joints or connecting rods of the motion arms relative to a same reference direction. For example, that a rotation angle of a joint (for example, a joint 1201a) of the first motion arm 12a relative to the beam 132 is less than a rotation angle of a joint (for example, a joint 1201b) of the second motion arm 12b relative to the beam 132 is determined based on an initial position order. That the first motion arm 12a and the second motion arm 12b satisfy the constraint of the predetermined relative position order relationship may be determined in response to determination that the rotation angle of the joint 1201a relative to the beam 132 is less than the rotation angle of the joint 1201b relative to the beam 132. Otherwise, that the first motion arm 12a and the second motion arm 12b do not satisfy the predetermined relative position order may be determined, and there may be an interference relationship between the first motion arm 12a and the second motion arm 12b.

In some embodiments, a predetermined point associated with a motion arm may include a fixed point on a connecting rod of the motion arm, a joint of the motion arm, or another point associated with the motion arm. For example, a predetermined point associated with the first motion arm 12a may be a predetermined joint (for example, the joint 1203a) of the first motion arm 12a, and a predetermined point associated with the second motion arm 12b may be a corresponding joint (for example, the joint 1203b) of the second motion arm 12b. In some embodiments, a distance between the joint 1203a of the first motion arm 12a and the joint 1203b of the second motion arm 12b may be determined based on a joint axis of the joint 1203a of the first motion arm 12a and a joint axis of the joint 1203b of the second motion arm 12b. In some embodiments, a predetermined point associated with the first motion arm 12a may be a fixed point on a predetermined connecting rod (for example, the connecting rod 121a) of the first motion arm 12a, and a predetermined point associated with the second motion arm 12b may be a fixed point on a corresponding connecting rod (for example, the connecting rod 121b) of the second motion arm 12b or on an adjacent connecting rod (for example, 123b). In some embodiments, a predetermined point associated with the first motion arm 12a may be a fixed point on a predetermined connecting rod (for example, a remote center of motion mechanism (RCM mechanism)) of the first motion arm 12a, and a predetermined point associated with the second motion arm 12b may be a projection point, on a horizontal plane, of an axis of a connecting rod (for example, the connecting rod 124b) of the second motion arm 12b. For example, when a distance between joint axes of the joint 1203a and the joint 1203b is greater than the safety distance, or a distance between predetermined points on the first motion arm 12a and the second motion arm 12b is greater than the safety distance, that the first motion arm 12a and the second motion arm 12b satisfy the constraint of safety distance between predetermined points may be determined. Otherwise, a distance between the predetermined points is less than the safety distance, and that there may be an interference relationship between the first motion arm 12a and the second motion arm 12b is determined. It should be understood that the safety distance may be a preset distance, and may include, but is not limited to, for example, 135 mm. It should be understood that the safety distance may alternatively be set based on a size of a joint or connecting rod. Safety distances between predetermined points corresponding to different joints or connecting rods may be different. It should be understood that the predetermined points associated with the first motion arm 12a and the second motion arm 12b may include, but are not limited to, examples shown in the foregoing embodiments.

In some embodiments, a predetermined line segment associated with a motion arm may include an edge or axis of a connecting rod of the motion arm, a joint axis of the motion arm, or another line segment associated with the motion arm. It should be understood that a minimum distance between two line segments is a shorter distance in a distance between two starting points of the two line segments and a distance between two ending points of the two line segments. For example, a predetermined line segment associated with the first motion arm 12a may be a predetermined connecting rod (for example, the connecting rod 121a) of the first motion arm 12b, and a predetermined line segment associated with the second motion arm 12b may be a predetermined connecting rod (for example, the connecting rod 122b) of the second motion arm 12b. In some embodiments, a predetermined line segment associated with the first motion arm 12a may be a predetermined connecting rod (for example, a connecting rod 125a) of the first motion arm 12a, and a predetermined line segment associated with the second motion arm 12b may be an edge, close to the connecting rod 125a, of a predetermined connecting rod (for example, a remote center of motion mechanism (RCM mechanism)) of the second motion arm 12b (for example, an edge, close to the connecting rod 125a, of a connecting rod 126a). In some embodiments, a predetermined line segment associated with the first motion arm 12a may be a line segment between an RCM point of the first motion arm 12a and a point on an extension line of a predetermined connecting rod (for example, a connecting rod 128a) of the first motion arm 12a, and a predetermined line segment associated with the second motion arm 12b may be an edge, close to the first motion arm 12a, of a predetermined connecting rod (for example, a connecting rod 128b) of the second motion arm 12b. In some embodiments, a predetermined line segment associated with the first motion arm 12a may be an edge (for example, an edge close to the second motion arm 12b) of a predetermined connecting rod (for example, a connecting rod 124a) of the first motion arm 12a, and a predetermined line segment associated with the second motion arm 12b may be an edge (for example, an edge close to the first motion arm 12a) of a corresponding connecting rod (for example, a connecting rod 124b) of the second motion arm 12b. In some embodiments, a predetermined line segment associated with the first motion arm 12a may be a joint axis of the first motion arm 12a, and a predetermined line segment associated with the second motion arm 12b may be a joint axis of the second motion arm 12b. In some embodiments, a predetermined line segment associated with the first motion arm 12a may be a line segment between a farther end of a connecting rod (for example, the connecting rod 125a) of the first motion arm 12a and a point of intersection of the joint axis (for example, an axis of a joint 1204a) of the first motion arm 12a and another joint axis (for example, an axis of a joint 1205a), and a predetermined line segment associated with the second motion arm 12b may be a line segment between a farther end of a connecting rod (for example, the connecting rod 125b) of the second motion arm 12b and a point of intersection of the joint axis (for example, an axis of a joint 1204b) of the second motion arm 12b and another joint axis (for example, an axis of a joint 1205b). For example, when a minimum distance between the connecting rod 121a and the connecting rod 122b is greater than the safety distance, or a minimum distance between the connecting rod 125a and the edge, close to the connecting rod 125a, of the RCM mechanism of the second motion arm 12b (for example, the edge, close to the connecting rod 125a, of the connecting rod 126b) is greater than the safety distance, or a minimum distance between the edge, close to the first motion arm 12a, of the connecting rod 128b and the line segment between the RCM point of the first motion arm 12a and the point on the extension line of the connecting rod 128a is greater than the safety distance, or a minimum distance between the edge, close to the second motion arm 12b, of the connecting rod 124a and the edge, close to the first motion arm 12a, of the connecting rod 124b is greater than the safety distance, or a minimum distance between two line segments, of which one being between the farther end of the connecting rod 125a and the point of intersection of the axes of the joint 1204a and the joint 1205a and the other one being between the farther end of the connecting rod 125b and the point of intersection of the axes of the joint 1204b and the joint 1205a, that the first motion arm 12a and the second motion arm 12b satisfy the constraint relationship of safety distance between predetermined line segments may be determined. Otherwise, a distance between the predetermined line segments is less than the safety distance, and that there may be an interference relationship between the first motion arm 12a and the second motion arm 12b is determined. It should be understood that the safety distance may include, but is not limited to, 135 mm, 120 mm, 60 mm, and the like. It should be understood that the safety distance may alternatively be set based on a size of a joint or connecting rod. Safety distances between predetermined points corresponding to different joints or connecting rods may be different. It should be understood that the predetermined line segments associated with the first motion arm 12a and the second motion arm 12b may include, but are not limited to, examples shown in the foregoing embodiments.

In some embodiments, when a difference between a joint value of one or more joints (for example, a joint value of the joint 1203a) of the first motion arm 12a and a joint value of a corresponding joint (for example, a joint value of the joint 1203b) of the second motion arm 12b is greater than a predetermined safety value (for example, a safety angle), that the first motion arm 12a and the second motion arm 12b satisfy a constraint relationship of safety angle between joints may be determined. Otherwise, a difference between joint values is less than the predetermined safety value, and that there may be an interference relationship between the first motion arm 12a and the second motion arm 12b is determined.

It should be understood that when the robot system includes three, four, or more motion arms, the constraint relationship may further be used to determine a possibility of interference between adjacent motion arms or motion arms that are close to each other. In some embodiments, comparison objects for the constraint relationship may be structures, prone to interfere with each other, of adjacent motion arms (for example, a predetermined line segment associated with the first motion arm 12a and a predetermined line segment associated with the second motion arm 12b, a predetermined point associated with the first motion arm 12a and a predetermined point associated with the second motion arm 12b, or one or more joints of the first motion arm 12a and a corresponding joint of the second motion arm 12b). Structures that never interfere with each other of a plurality of motion arms may be excluded from comparison objects for the constraint relationship, such that not all structures on adjacent motion arms need to undergo comparison, thereby reducing the amount of calculation during comparison for the constraint relationship, and improving working efficiency of the system.

Figure 8:
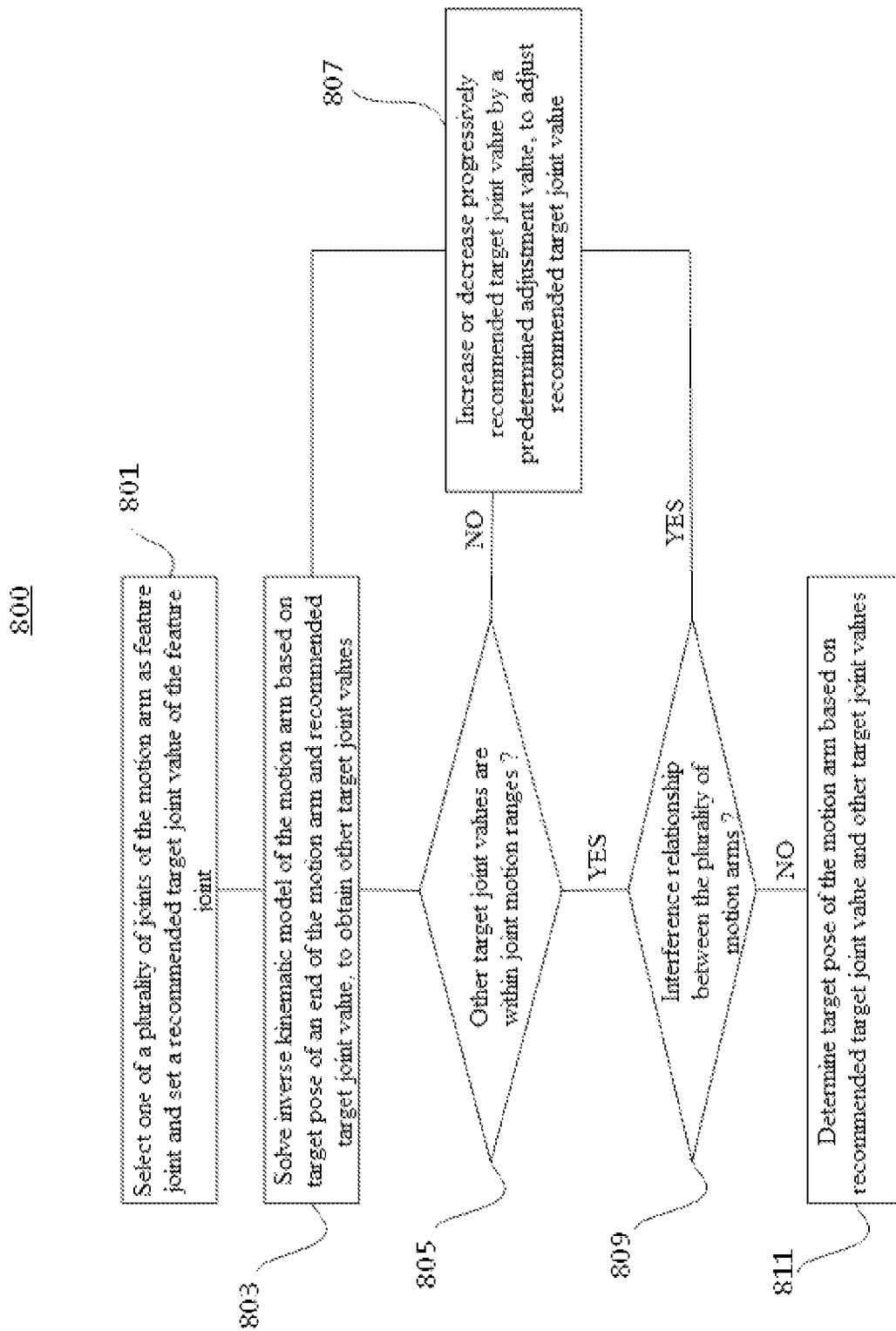
FIG. 8 is a flowchart of a method for determining a target pose of a motion arm according to some embodiments of the present disclosure.

FIG. 8 is a flowchart of a method 800 for determining a target pose of a motion arm according to some embodiments of the present disclosure. For example, the method 800 may be used to implement step 705 of determining a first target pose of the first motion arm based on a first current pose of the first motion arm and the target pose of the first end and a second target pose of the second motion arm based on a second current pose of the second motion arm and the target pose of the second end, as shown in FIG. 7. The method 800 may be performed by a control apparatus (for example, a control apparatus 11) of a robot system 10. The control apparatus 11 may be mounted on a computing device. The method 800 may be implemented by software, firmware, and/or hardware.

As shown in FIG. 8, in step 801, the method 800 may include: selecting one of a plurality of joints of the motion arm as a feature joint and setting a recommended target joint value of the feature joint. In some embodiments, the second motion arm 12b is used as an example. One of a plurality of joints of the second motion arm 12b is selected as a feature joint, and a recommended target joint value of the feature joint is preset. In some embodiments, a feature joint of the motion arm may be a joint, prone to collide with an adjacent motion arm, in a plurality of joints. For example, the selected feature joint may be a joint, for example, a joint 1205b or 1206b shown in FIG. 3, prone to collide with the first motion arm 12a, in the plurality of joints of the second motion arm 12b. It should be understood that when the robot system 10 includes a plurality of motion arms (for example, three or four motion arms), recommended target joint values of feature joints of different motion arms may be different. In some embodiments, the recommended target joint value may be predetermined.

In step 803, an inverse kinematic model of the motion arm is solved based on a target pose of an end of the motion arm and a recommended target joint value, to obtain other target joint values of the motion arm. It should be understood that the other target joint values include target joint values of all joints other than a feature joint of the motion arm. For example, an inverse kinematic model of the second motion arm 12b is solved based on a target pose of an end arm 128b of the second motion arm 12b and a recommended target joint value of a recommended joint (for example, 1205b), to obtain other target joint values of the second motion arm 12b.

In some embodiments, the method 800 may further include step 805. In step 805, whether the other target joint values of the motion arm are within joint motion ranges of corresponding joints is determined. It should be understood that each joint of the motion arm has a specific motion range, and the joint motion range of each joint is a range between a minimum limit joint value and a maximum limit joint value of the corresponding joint. The minimum limit joint value and the maximum limit joint value may be beyond the range. For example, a motion range of a joint is between 18 degrees and 45 degrees, a motion range of another joint is between 45 degrees and 90 degrees, and a motion range of still another joint is between −90 degrees and −45 degrees, and so on.

In some embodiments, the method 800 may further include step 807. In step 807, the recommended target joint value is increased or decreased progressively by a predetermined adjustment value, to adjust the recommended target joint value of the motion arm, and step 803 of the method 800 is performed again. For example, the recommended target joint value is increased or decreased progressively by a predetermined adjustment value in response to determination that at least one of the other target joint values of the second motion arm 12b is beyond the joint motion range of the corresponding joint, to adjust the recommended target joint value of the second motion arm 12b. In some embodiments, the adjustment value may be set to 0.2 degrees, 0.5 degrees, or the like, to adjust the recommended target joint value. It should be understood that 0.2 degrees or 0.5 degrees is merely an example, and the adjustment value may alternatively be set to another value. The recommended target joint value is increased or decreased progressively by the predetermined adjustment value till there is a solution or the joint motion range (that may not include a joint limit value) of the feature joint is reached. For example, a solution may mean that the recommended target joint value is within the joint motion range of the feature joint and all the other target joint values are within the joint motion range of the corresponding joint.

In some embodiments, the method 800 may further include the following steps: determining whether an adjusted recommended target joint value is within a joint motion range of a feature joint; selecting the adjusted recommended target joint value as a recommended target joint value in response to determination that the adjusted recommended target joint value is within the joint motion range of the feature joint, and performing step 803 again.

In some embodiments, the method 800 may further include step 811. In step 811, the target pose of the motion arm is determined based on the recommended target joint value and the other target joint values of the motion arm. For example, the target pose of the second motion arm 12b is determined based on the recommended target joint value and the other target joint values of the second motion arm 12b in response to determination that all the other target joint values of the second motion arm 12b are within the joint motion range of the corresponding joint. For example, a set of the recommended target joint value and the other target joints may be selected as a target joint value of the second motion arm 12b. The target pose of the second motion arm 12b may be determined by determining the target joint value of the second motion arm 12b. It should be understood that a target pose of the first motion arm 12a may further be determined according to the method 800.

In some embodiments, the method 800 may further include step 809 between step 805 to step 811. In step 809, whether there is an interference relationship between the plurality of motion arms is determined. For example, whether there is an interference relationship between the second motion arm 12b and an adjacent motion arm (for example, the first motion arm 12a) is determined based on a constraint relationship in response to determination that all the other target joint values of the second motion arm 12b are within the joint motion range of the corresponding joint. In some embodiments, step 811 is performed in response to determination that there is no interference relationship between the plurality of motion arms. For example, the target pose of the second motion arm 12b is determined based on the recommended target joint value and the other target joint values of the second motion arm 12b in response to determination that there is no interference relationship between the second motion arm 12b and the first motion arm 12a. In some embodiments, step 807 of the method 800 is performed in response to determination that there is an interference relationship between the plurality of motion arms. For example, the recommended target joint value of the second motion arm 12b is increased or decreased progressively by a predetermined adjustment value in response to determination that there is an interference relationship between the second motion arm 12b and the first motion arm 12a, to adjust the recommended target joint value of the second motion arm 12b.

In some embodiments, when there are a plurality of sets of solutions to the recommended target joint value and the other target joint values that satisfy the constraint (for example, when there are a plurality of groups of solutions to the target joint value of the second motion arm 12b that satisfy the constraint), a set of solutions in which the joints of the second motion arm 12b are least likely to interfere with the first motion arm 12a is output as unique solution and used as the target joint value of the second motion arm 12b.

Figure 9:
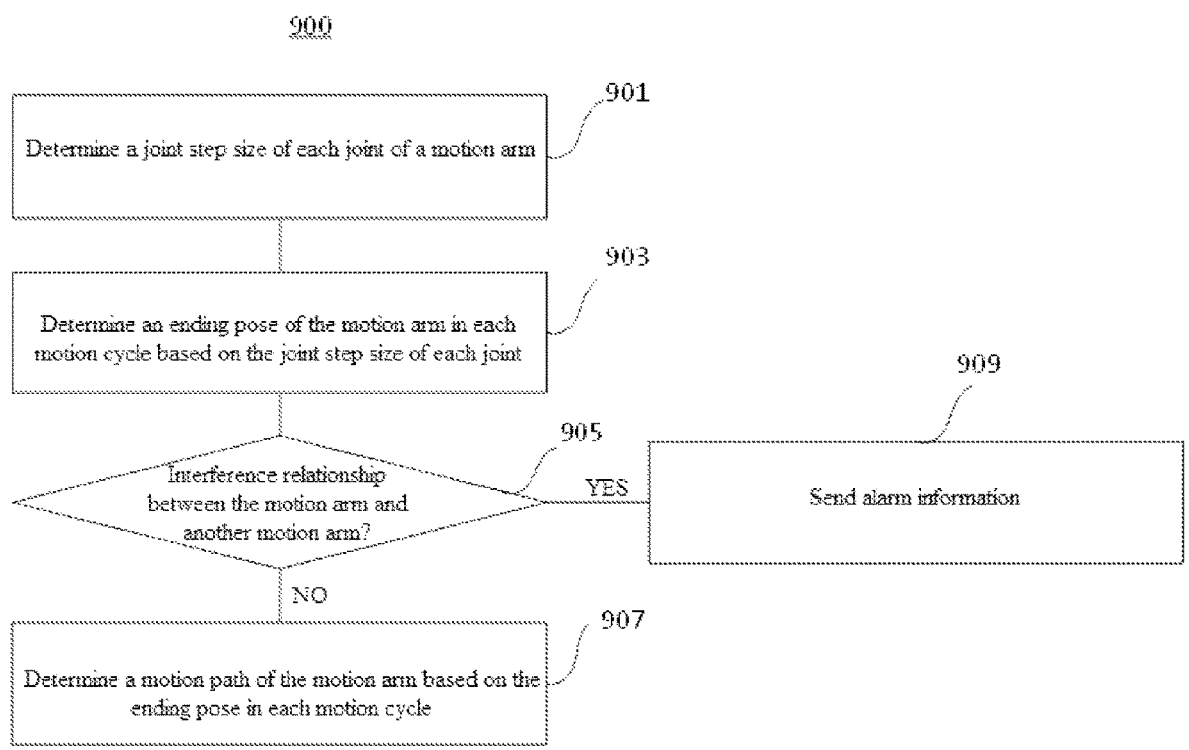
FIG. 9 is a flowchart of a method for controlling a motion path of a motion arm according to some embodiments of the present disclosure.

FIG. 9 is a flowchart of a method 900 for determining a motion path of a motion arm from an initial pose to a target pose according to some embodiments of the present disclosure. In some embodiments, the method 900 may be used to implement step 709 shown in FIG. 7. The method 900 may be performed by a control apparatus (for example, a control apparatus 11) of a robot system 10. The control apparatus 11 may be mounted on a computing device. The method 900 may be implemented by software, firmware, and/or hardware.

Figure 10:
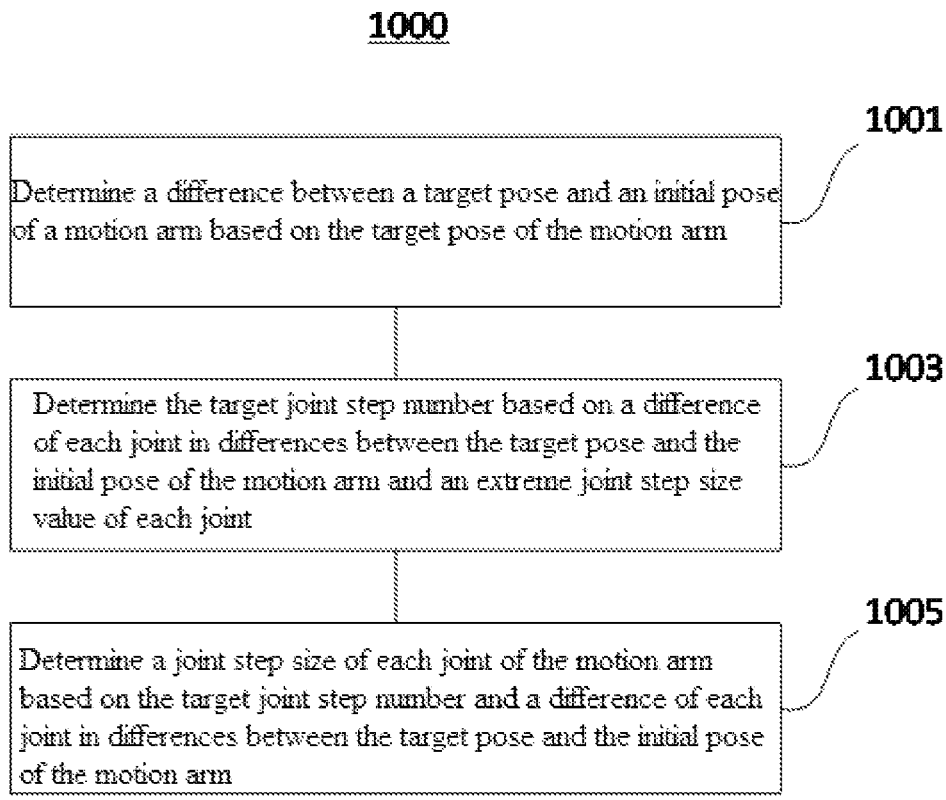
FIG. 10 is a flowchart of a method for determining a joint step size of each joint of a motion arm according to some embodiments of the present disclosure.

As shown in FIG. 9, in step 901, a joint step size of each joint of a motion arm is determined. In some embodiments, a process in which the motion arm is controlled to move to the target pose may include one or more motion cycles. Each joint step size corresponds to a motion step size of the motion arm in a single motion cycle. In an implementation, a single motion cycle may be 80 ms. In some embodiments, a joint step size of each joint may indicate an angle by which the corresponding joint rotates about a joint axis of the joint in each motion cycle. For example, a motion step size of the motion arm in a single motion cycle may be preset, where the motion step size of the motion arm may be a set of joint step sizes of the plurality of joints of the motion arm. In some embodiments, as shown in FIG. 10, the method 1000 may be used to determine a step size of each joint of a motion arm.

In step 903, an ending pose of the motion arm in each motion cycle is determined based on the joint step size of each joint. In some embodiments, an ending pose in each motion cycle of a plurality of motion cycles may be determined between the initial pose and the target pose of the motion arm based on an interpolation method. For example, the first motion arm 12a is used as an example. When a current motion cycle is the first motion cycle, a current pose of the first motion arm 12a is an initial pose of the first motion arm 12a. When the current motion cycle is not the first motion cycle, the current pose of the first motion arm 12a is an ending pose in the previous motion cycle. An ending joint value of each joint of the first motion arm 12a in the current cycle is determined based on the current pose of the first motion arm 12a and a joint step size corresponding to each joint of the first motion arm 12a.

In some embodiments, the method 900 further includes step 905. In step 905, whether there is an interference relationship between the motion arm and another motion arm is determined based on the ending pose in each motion cycle. For example, whether there is an interference relationship, for example, a collision, between the first motion arm 12a and the second motion arm 12b or another motion arm (for example, a motion arm that is near) is determined based on the ending pose in the current cycle.

In step 907, a motion path of the motion arm is determined based on the ending pose in each motion cycle. For example, the ending pose in each motion cycle is determined as the motion path in response to determination that there is no interference relationship between the motion arm and the another motion arm in a process in which the motion arm moves from the initial pose to the target pose.

In step 909, alarm information is sent. For example, the alarm information may be sent in response to determination that there is an interference relationship between the motion arm and the another motion arm. For example, a possibility of interference between the first motion arm 12a and the second motion arm 12b is determined, and the alarm information may be sent in response to determination that there is a collision between another motion arm and at least one of the first motion arm 12a and the second motion arm 12b.

FIG. 10 is a flowchart of a method 1000 for determining a joint step size of each joint of a motion arm according to some embodiments of the present disclosure. In some embodiments, the method 1000 may be used to implement step 901 of determining a joint step size of each joint of a motion arm, as shown in FIG. 9. The method 1000 may be performed by a control apparatus (for example, a control apparatus 11) of a robot system 10. The control apparatus 11 may be mounted on a computing device. The method 1000 may be implemented by software, firmware, and/or hardware.

As shown in FIG. 10, in step 1001, a difference between a target pose and an initial pose of the motion arm is determined based on the target pose of the motion arm. For example, a pose of the motion arm may be represented by a set of joint values of a plurality of joints of the motion arm. A difference between the target pose and the initial pose of the motion arm may be represented by a set of differences between a joint value of a corresponding joint of the motion arm in the target pose and a joint value of the corresponding joint in the initial pose.

In step 1003, the target joint step number is determined based on a difference of each joint in differences between the target pose and the initial pose of the motion arm and an extreme joint step size value of each joint. It should be understood that a joint step size may indicate an angle by which a joint rotates about a joint axis of the joint in each motion cycle. An extreme step size value may refer to a maximum angle by which a joint rotates about a joint axis of the joint in each motion cycle. For example, the step number of each joint of the first motion arm 12a is determined based on an extreme step size value of each joint and a difference of each joint in differences between the target pose and the initial pose of the motion arm (for example, the first motion arm 12a). A maximum step number of each joint may be selected as the target joint step number.

In step 1005, a joint step size of each joint of the motion arm is determined based on the target joint step number and a difference of each joint in differences between the target pose and the initial pose of the motion arm. For example, a joint step size of each joint of the first motion arm 12a (or the second motion arm 12b) is obtained by calculation of dividing a difference of each joint in differences between the target pose and the initial pose of the first motion arm 12a (or the second motion arm 12b) by the target joint step number.

Figure 11:
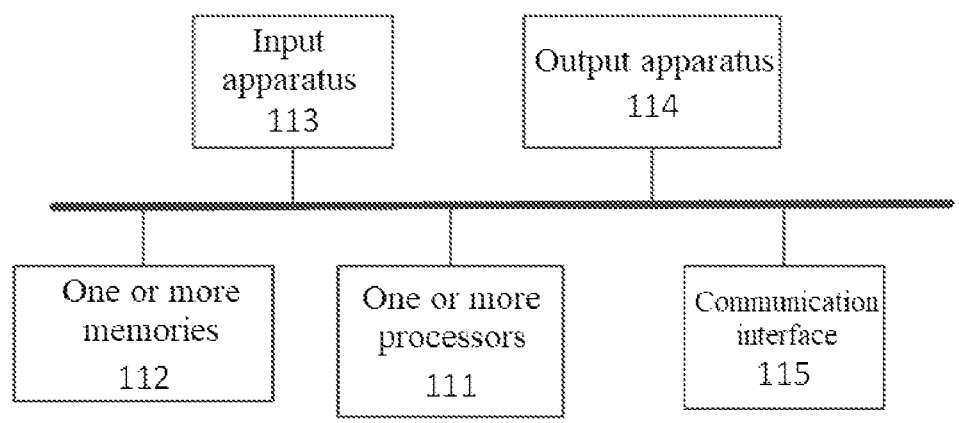
FIG. 11 is a schematic diagram of an architecture of a control apparatus according to some embodiments of the present disclosure.

FIG. 11 is a schematic diagram of an architecture of a control apparatus 11 of a robot system 10 according to an embodiment of the present disclosure. In some embodiments, as shown in FIG. 11, the control apparatus 11 may include an input apparatus 113, an output apparatus 114, one or more memories 112, one or more processors 111, and a communication interface 115. In some embodiments, the control apparatus 11 may not include an output apparatus.

In some embodiments, the input apparatus 113 may include, but is not limited to, apparatuses such as a button, a keyboard, a touch screen, and a microphone. The input apparatus may be used for: receiving an operating command directly from a user; or receiving an operating instruction from a user, so that the control apparatus can obtain a specific operating command based on the operating instruction. The operating command may include, for example, a command requiring that a relative end pose relationship between the second end arm 128b and the first end arm 128a remains unchanged during motion. In some embodiments, the input apparatus 113 may further be used for receiving setting information from a user, for example, setting information about the type of the current surgery, the configuration of the auxiliary connection apparatus, and the relative pose model.

In some embodiments, the output apparatus 114 may include, but is not limited to, a display, a loudspeaker, and an indicator, and may be configured so as to be used for: indicating statuses of various components of the robot system 10, and outputting an alarm signal, and so on.

In some embodiments, a computer program that can be run on the processor 111 may be stored in the memory 112. The processor 111 executes the computer program to implement the control method described in the foregoing embodiments. There may be one or more memories 112 and one or more processors 111. The communication interface 115 is used for communication between the control apparatus 11 (for example, the processor 111 of the control apparatus 11) and a peripheral device. In the present disclosure, the control apparatus 11 may communicate, through, for example, the communication interface 115, with a motor disposed at each joint of each motion arm (for example, the first motion arm 12a and the second motion arm 12b), to instruct each motion arm to move to a corresponding target position. The control apparatus 11 may further communicate, through, for example, the communication interface 115, with a sensor at each joint of the motion arm, to receive a joint value of each joint of the motion arm. In an example of the present disclosure, the communication interface 115 may be a CAN bus communication interface and enables the control apparatus 11 to be connected to and communicate with the motor and the sensor disposed at each joint through the CAN bus.

As shown in FIG. 11, the input apparatus 113, the output apparatus 114, the memory 112, the processor 111, and the communication interface 115 may be connected to each other by using a bus, to implement intercommunication. The bus may be an industry standard architecture (ISA) bus, a peripheral component interconnect (PCI) bus, an extended industry standard architecture (EISA) bus, or the like.

In some embodiments, the processor 111 may be various types of general-purpose processors, for example, a central processing unit (CPU) or a digital signal processor (DSP). This is not limited herein.

In some embodiments, the control apparatus 11 may be integrated into the base 131 (for example, at the bottom of the base 131) to save space. But in actual application, the control apparatus 11 may alternatively be separate from the base 131, or one part of the control apparatus 11 may be integrated with the base 131, and the other part is separate from the base 131. Alternatively, the control apparatus 11 may be disposed in another manner for being communicatively connected to each motion arm and controlling each motion arm.

In some embodiments, the present disclosure provides a computer-readable storage medium that may include at least one instruction, where the at least one instruction is executed by a processor to perform the control method according to any of the foregoing embodiments.

In some embodiments, the present disclosure provides a computer system that may include a non-volatile storage medium and at least one processor. The non-volatile storage medium may include at least one instruction. The processor is configured to execute the at least one instruction, such that the processor is configured to perform the control method according to any of the foregoing embodiments.

In some embodiments, the computer-readable storage medium may be a tangible device that may keep and store instructions to be used by an instruction execution device. The computer-readable storage medium may be, but is not limited to, for example, an electrical storage device, a magnetic storage device, an optical storage device, an electromagnetic storage device, a semiconductor storage device, or any combination of the foregoing devices.

In some embodiments, the computer-readable storage medium may include, but is not limited to: a portable computer disk, a hard disk, a read-only memory (ROM), a random access memory (RAM), an erasable programmable read-only memory (EPROM), an electrically erasable programmable read-only memory (EEPROM), a flash memory or another solid storage technology, a CD-ROM, a digital versatile disc (DVD), an HD-DVD, a blu-ray or another optical storage device, a magnetic tape, a disk storage or another magnetic storage device, or any other medium that can be used to store necessary information and that can be accessed by a computer. The medium stores a computer-executable instruction, and when the computer-executable instruction is run by a machine (for example, a computer device), the machine performs the control method in the present disclosure. It should be understood that the computer device may include a personal computer, a server, a network device, and the like.

Some embodiments of the present disclosure can optimize placement of a motion arm during preoperative preparations. A target pose of a motion arm may be calculated based on a real-time pose of another motion arm, and the motion arm may be controlled to move to the target pose, thereby implementing a high level of automation during preoperative placement.

According to some embodiments of the present disclosure, after the target pose of the motion arm is calculated in real time, the motion arm can further be controlled to move to a target position precisely, quickly, and safely in a specific planned manner, thereby achieving highly efficient and safe preoperative preparations.

According to some embodiments of the present disclosure, the ends of the plurality of motion arms move as a whole, and the relative pose relationship between the ends of the plurality of motion arms can remain unchanged during the motion to control the plurality of motion arms to move quickly and accurately. During a surgery, through the synchronous motion of the plurality of motion arms, fast adjustments of poses of surgical instruments on the plurality of motion arms may be achieved, thereby reducing difficulties for a user (for example, a surgeon) to operate, and improving working efficiency before or during the surgery.

The following is further disclosed in the present disclosure:

Item 1. A control method for a robot system, where the robot system includes a plurality of motion arms, the plurality of motion arms include a first motion arm and a second motion arm, and the control method includes:
determining a motion mode of a first end of the first motion arm and a second end of the second motion arm of the robot system, where the motion mode includes synchronous motion of the first end of the first motion arm and the second end of the second motion arm;
determining a first motion path of the first motion arm and a second motion path of the second motion arm based on the motion mode and a relative end pose relationship between the first end of the first motion arm and the second end of the second motion arm; and
controlling, based on the first motion path and the second motion path, the first motion arm and the second motion arm to move, such that the first end of the first motion arm and the second end of the second motion arm move in the motion mode, and the relative end pose relationship remains unchanged during the motion.

Item 2. The control method according to item 1, further including:
determining the relative end pose relationship between the first end of the first motion arm and the second end of the second motion arm based on a type of a current surgery or configuration of an auxiliary connection apparatus.

Item 3. The control method according to any one of items 1 and 2, where determining the first motion path of the first motion arm and the second motion path of the second motion arm based on the motion mode and the relative end pose relationship includes:
determining a target pose of the first end of the first motion arm based on the motion mode; and
determining a target pose of the second end of the second motion arm based on the motion mode.

Item 4. The control method according to item 3, where the target pose of the first end includes one of the following:
a target position and a target posture of an end arm of the first motion arm;
a target position and a target posture of a remote center of motion mechanism (RCM mechanism) of the first motion arm; or
a target position and a target posture of an end, for being connected to an auxiliary connection apparatus, of the first motion arm; or
the target pose of the second end includes one of the following:
a target position and a target posture of an end arm of the second motion arm;
a target position and a target posture of a remote center of motion mechanism (RCM mechanism) of the second motion arm; or
a target position and a target posture of an end, for being connected to an auxiliary connection apparatus, of the second motion arm.

Item 5. The control method according to any one of items 3 and 4, further including: determining a first target pose of the first motion arm based on a first current pose of the first motion arm and the target pose of the first end; and
determining a second target pose of the second motion arm based on a second current pose of the second motion arm and the target pose of the second end.

Item 6. The control method according to item 5, where the determining a first target pose of the first motion arm based on a first current pose of the first motion arm and the target pose of the first end includes:
selecting one of a plurality of joints of the first motion arm as a first feature joint;
setting a first recommended target joint value of the first feature joint; and
determining other target joint values of the first motion arm based on the target pose of the first end and the first recommended target joint value; or
the determining a second target pose of the second motion arm based on a second current pose of the second motion arm and the target pose of the second end includes:
selecting one of a plurality of joints of the second motion arm as a second feature joint;
setting a second recommended target joint value of the second feature joint; and
determining other target joint values of the second motion arm based on the target pose of the second end and the second recommended target joint value.

Item 7. The control method according to item 6, further including:
determining whether the other target joint values of the first motion arm are within joint motion ranges of corresponding joints; and
increasing or decreasing progressively the first recommended target joint value by a predetermined adjustment value in response to determination that at least one of the other target joint values of the first motion arm is beyond the joint motion range of the corresponding joint, to adjust the first recommended target joint value; or
determining whether the other target joint values of the second motion arm are within joint motion ranges of corresponding joints; and
increasing or decreasing progressively the second recommended target joint value by a predetermined adjustment value in response to determination that at least one of the other target joint values of the second motion arm is beyond the joint motion range of the corresponding joint, to adjust the second recommended target joint value.

Item 8. The control method according to item 7, further including:
determining the first target pose of the first motion arm based on the first recommended target joint value and the other target joint values in response to determination that all the other target joint values of the first motion arm are within the joint motion range of the corresponding joint; or
determining the second target pose of the second motion arm based on the second recommended target joint value and the other target joint values in response to determination that all the other target joint values of the second motion arm are within the joint motion range of the corresponding joint.

Item 9. The control method according to any one of items 7 and 8, further including: determining the other target joint values of the first motion arm based on the target pose of the first end and an adjusted first recommended target joint value; or determining the other target joint values of the second motion arm based on the target pose of the second end and an adjusted second recommended target joint value.

Item 10. The control method according to any one of items 6 to 9, further including:
determining whether there is an interference relationship between the second motion arm and the first motion arm; and
adjusting the first recommended target joint value or the second recommended target joint value in response to determination that there is an interference relationship between the second motion arm and the first motion arm.

Item 11. The control method according to any one of items 6 to 10, where the first feature joint is a joint, prone to collide with another motion arm in the plurality of motion arms, in the plurality of joints of the first motion arm; or
the second feature joint is a joint, prone to collide with another motion arm in the plurality of motion arms, in the plurality of joints of the second motion arm.

Item 12. The control method according to any one of items 1 to 11, further including:
determining whether there is an interference relationship between the first motion arm and the second motion arm based on a constraint relationship; and
controlling the first motion arm and the second motion arm to stop moving, or sending alarm information, in response to determination that there is an interference relationship between the first motion arm and the second motion arm.

Item 13. The control method according to item 12, where the determining whether there is an interference relationship between the first motion arm and the second motion arm includes:
determining that there is no interference relationship between the first motion arm and the second motion arm based on the constraint relationship that is satisfied; and
determining that there is an interference relationship between the first motion arm and the second motion arm based on the constraint relationship that is not satisfied.

Item 14. The control method according to item 13, where the constraint relationship includes at least one of the following:
a relative position order relationship between the first motion arm and the second motion arm conforms to a predetermined relative position order relationship;
a distance between a predetermined point associated with the first motion arm and a predetermined point associated with the second motion arm is greater than a predetermined safety distance;
a minimum distance between a predetermined line segment associated with the first motion arm and a predetermined line segment associated with the second motion arm is greater than a predetermined line segment safety distance; or
a difference between a joint value of one or more joints of the first motion arm and a joint value of a corresponding joint of the second motion arm is greater than a predetermined safety value.

Item 15. The control method according to any one of items 1 to 14, further including:
determining the first motion path of the first motion arm and the second motion path of the second motion arm based on an interpolation method.

Item 16. The control method according to item 15, including: for each motion arm, determining a joint step size of each joint of the motion arm based on a target pose and an initial pose of the motion arm.

Item 17. The control method according to item 16, including: for each motion arm, determining an ending pose of the motion arm in each motion cycle based on the joint step size of each joint of the motion arm; and
determining a motion path of the motion arm based on the ending pose in each motion cycle.

Item 18. The control method according to any one of items 1 to 17, where the synchronous motion includes: synchronous translation, synchronous rotation, or a combination of synchronous translation and synchronous rotation.

Item 19. A robot system, including:
a plurality of motion arms, where the plurality of motion arms include:
a first motion arm;
a second motion arm; and
a control apparatus configured to perform the control method according to any one of items 1 to item 18.

Item 20. The robot system according to item 19, where the robot system further includes an auxiliary connection apparatus, where the auxiliary connection apparatus at least includes a first cannula for being connected to the first end and a second cannula for being connected to the second end, and the relative end pose relationship is determined based on shapes of and a relative position relationship between the first cannula and the second cannula.

Item 21. The robot system according to item 20, where a first auxiliary connection portion is provided on the first cannula, and a second auxiliary connection portion is provided on the second cannula; and a first arm connection portion for being connected to the first auxiliary connection portion is provided at the end of the first motion arm, and a second arm connection portion for being connected to the second auxiliary connection portion is provided at the end of the second motion arm.

Item 22. A computer-readable storage medium, including one or more instructions, where the instructions are executed by a processor to perform the control method according to any one of items 1 to 18.

Item 23. A computer system, including:
a memory for storing at least one instruction; and
a processor configured to execute the at least one instruction, to perform the control method according to any one of items 1 to 18.

It should be noted that the foregoing descriptions are merely exemplary embodiments of the present disclosure and technical principles applied thereto. Those skilled in the art can understand that the present disclosure is not limited to the specific embodiments herein, and various obvious modifications, changes and substitutions can be made by those skilled in the art without departing from the protection scope of the present disclosure. Therefore, the present disclosure is described in detail by the foregoing embodiments, but the present disclosure is not limited to the foregoing embodiments. Other equivalent embodiments may also be included without departing from the concept of the present disclosure. Therefore, the scope of the present disclosure depends on the appended claims.

The invention claimed is:

1. A control method for a robot system, wherein the robot system comprises a plurality of motion arms, the plurality of motion arms comprise a first motion arm and a second motion arm, and the control method comprises:
determining a motion mode of a first end of the first motion arm and a second end of the second motion arm of the robot system, wherein the motion mode comprises synchronous motion of the first end of the first motion arm and the second end of the second motion arm;

determining a first motion path of the first motion arm and a second motion path of the second motion arm based on the motion mode and a relative end pose relationship between the first end of the first motion arm and the second end of the second motion arm; and controlling, based on the first motion path and the second motion path, the first motion arm and the second motion arm to move, such that the first end of the first motion arm and the second end of the second motion arm move in the motion mode, and the relative end pose relationship remains unchanged during the motion, wherein determining the first motion path of the first motion arm and the second motion path of the second motion arm based on the motion mode and the relative end pose relationship comprises:

determining a target pose of the first end of the first motion arm based on the motion mode; and determining a target pose of the second end of the second motion arm based on the motion mode, wherein the control method further comprises:

determining a first target pose of the first motion arm based on a first current pose of the first motion arm and the target pose of the first end; and determining a second target pose of the second motion arm based on a second current pose of the second motion arm and the target pose of the second end, and wherein determining the first target pose of the first motion arm based on the first current pose of the first motion arm and the target pose of the first end comprises:

selecting one of a plurality of joints of the first motion arm as a first feature joint;

setting a first recommended target joint value of the first feature joint; and determining other target joint values of the first motion arm based on the target pose of the first end and the first recommended target joint value, or wherein determining the second target pose of the second motion arm based on the second current pose of the second motion arm and the target pose of the second end comprises:

selecting one of a plurality of joints of the second motion arm as a second feature joint;

setting a second recommended target joint value of the second feature joint; and determining other target joint values of the second motion arm based on the target pose of the second end and the second recommended target joint value.

2. The control method according to claim 1, further comprising:

determining the relative end pose relationship between the first end of the first motion arm and the second end of the second motion arm based on a type of a current surgery or configuration of an auxiliary connection apparatus.

3. The control method according to claim 1, wherein:

the target pose of the first end comprises one of the following:

a target position and a target posture of an end arm of the first motion arm;

a target position and a target posture of a remote center of motion (RCM) mechanism of the first motion arm; or a target position and a target posture of an end, for being connected to an auxiliary connection apparatus, of the first motion arm; or the target pose of the second end comprises one of the following:

a target position and a target posture of an end arm of the second motion arm;

a target position and a target posture of a remote center of motion (RCM) mechanism of the second motion arm; or a target position and a target posture of an end, for being connected to an auxiliary connection apparatus, of the second motion arm.

4. The control method according to claim 1, further comprising:

determining whether the other target joint values of the first motion arm are within joint motion ranges of corresponding joints; and increasing or decreasing progressively the first recommended target joint value by a predetermined adjustment value in response to determining that at least one of the other target joint values of the first motion arm is beyond the joint motion range of the corresponding joint, to adjust the first recommended target joint value; or determining whether the other target joint values of the second motion arm are within joint motion ranges of corresponding joints; and increasing or decreasing progressively the second recommended target joint value by a predetermined adjustment value in response to determining that at least one of the other target joint values of the second motion arm is beyond the joint motion range of the corresponding joint, to adjust the second recommended target joint value.

5. The control method according to claim 4, further comprising:

determining the other target joint values of the first motion arm based on the target pose of the first end and an adjusted first recommended target joint value; or determining the other target joint values of the second motion arm based on the target pose of the second end and an adjusted second recommended target joint value.

6. The control method according to claim 1, further comprising:

determining whether there is an interference relationship between the second motion arm and the first motion arm; and adjusting the first recommended target joint value or the second recommended target joint value in response to determining that there is the interference relationship between the second motion arm and the first motion arm.

7. The control method according to claim 1, wherein:

the first feature joint is a joint, prone to collide with another motion arm in the plurality of motion arms, in the plurality of joints of the first motion arm; or the second feature joint is a joint, prone to collide with another motion arm in the plurality of motion arms, in the plurality of joints of the second motion arm.

8. The control method according to claim 1, further comprising:
    determining, based on a constraint relationship, whether there is an interference relationship between the first motion arm and the second motion arm; and
    controlling the first motion arm and the second motion arm to stop moving, or sending alarm information, in response to determining that there is the interference relationship between the first motion arm and the second motion arm.

9. The control method according to claim 8, wherein the constraint relationship comprises at least one of the following:
    a relative position order relationship between the first motion arm and the second motion arm conforming to a predetermined relative position order relationship;
    a distance between a predetermined point associated with the first motion arm and a predetermined point associated with the second motion arm being greater than a predetermined safety distance;
    a minimum distance between a predetermined line segment associated with the first motion arm and a predetermined line segment associated with the second motion arm being greater than a predetermined line segment safety distance; or
    a difference between a joint value of one or more joints of the first motion arm and a joint value of a corresponding joint of the second motion arm being greater than a predetermined safety value.

10. The control method according to claim 1, comprising:
    determining the first motion path of the first motion arm and the second motion path of the second motion arm based on an interpolation method.

11. The control method according to claim 10, comprising:
    for each motion arm, determining a joint step size of each joint of the motion arm based on a target pose and an initial pose of the motion arm.

12. The control method according to claim 11, comprising:
    determining an ending pose of the motion arm in each motion cycle based on the joint step size of each joint of the motion arm; and
    determining a motion path of the motion arm based on the ending pose in each motion cycle.

13. The control method according to claim 1, wherein the synchronous motion comprises synchronous translation, synchronous rotation, or a combination of synchronous translation and synchronous rotation.

14. A robot system, comprising:
    a plurality of motion arms, wherein the plurality of motion arms comprise:
        a first motion arm;
        a second motion arm; and
    a control apparatus configured to:
        determine a motion mode of a first end of the first motion arm and a second end of the second motion arm of the robot system, wherein the motion mode comprises synchronous motion of the first end of the first motion arm and the second end of the second motion arm;
        determine a first motion path of the first motion arm and a second motion path of the second motion arm based on the motion mode and a relative end pose relationship between the first end of the first motion arm and the second end of the second motion arm; and
        control, based on the first motion path and the second motion path, the first motion arm and the second motion arm to move, such that the first end of the first motion arm and the second end of the second motion arm move in the motion mode, and the relative end pose relationship remains unchanged during the motion,
    wherein to determine the first motion path of the first motion arm and the second motion path of the second motion arm based on the motion mode and the relative end pose relationship, the control apparatus is further configured to:
        determine a target pose of the first end of the first motion arm based on the motion mode; and
        determine a target pose of the second end of the second motion arm based on the motion mode,
    wherein the control apparatus is further configured to:
        determine a first target pose of the first motion arm based on a first current pose of the first motion arm and the target pose of the first end; and
        determine a second target pose of the second motion arm based on a second current pose of the second motion arm and the target pose of the second end, and
    wherein to determine the first target pose of the first motion arm based on the first current pose of the first motion arm and the target pose of the first end, the control apparatus is further configured to:
        select one of a plurality of joints of the first motion arm as a first feature joint;
        set a first recommended target joint value of the first feature joint; and
        determine other target joint values of the first motion arm based on the target pose of the first end and the first recommended target joint value, or
    wherein to determine the second target pose of the second motion arm based on the second current pose of the second motion arm and the target pose of the second end, the control apparatus is further configured to:
        select one of a plurality of joints of the second motion arm as a second feature joint;
        set a second recommended target joint value of the second feature joint; and
        determine other target joint values of the second motion arm based on the target pose of the second end and the second recommended target joint value.

15. The robot system according to claim 14, wherein the robot system further comprises an auxiliary connection apparatus, wherein the auxiliary connection apparatus at least comprises a first cannula for being connected to the first end and a second cannula for being connected to the second end, and
    the relative end pose relationship is determined based on shapes of and a relative position relationship between the first cannula and the second cannula.

16. The robot system according to claim 15, wherein a first auxiliary connection portion is provided on the first cannula, and a second auxiliary connection portion is provided on the second cannula; and
    a first arm connection portion for being connected to the first auxiliary connection portion is provided at the end of the first motion arm, and a second arm connection portion for being connected to the second auxiliary connection portion is provided at the end of the second motion arm.

17. A non-transitory computer-readable storage medium comprising one or more instructions, wherein the instructions are executed by a processor to perform a control method for a robot system, the robot system comprises a plurality of motion arms, the plurality of motion arms comprise a first motion arm and a second motion arm, and the control method comprises:
- determining a motion mode of a first end of the first motion arm and a second end of the second motion arm of the robot system, wherein the motion mode comprises synchronous motion of the first end of the first motion arm and the second end of the second motion arm;
- determining a first motion path of the first motion arm and a second motion path of the second motion arm based on the motion mode and a relative end pose relationship between the first end of the first motion arm and the second end of the second motion arm; and
- controlling, based on the first motion path and the second motion path, the first motion arm and the second motion arm to move, such that the first end of the first motion arm and the second end of the second motion arm move in the motion mode, and the relative end pose relationship remains unchanged during the motion,
- wherein determining the first motion path of the first motion arm and the second motion path of the second motion arm based on the motion mode and the relative end pose relationship comprises:
  - determining a target pose of the first end of the first motion arm based on the motion mode; and
  - determining a target pose of the second end of the second motion arm based on the motion mode,
- wherein the control method further comprises:
  - determining a first target pose of the first motion arm based on a first current pose of the first motion arm and the target pose of the first end; and
  - determining a second target pose of the second motion arm based on a second current pose of the second motion arm and the target pose of the second end, and
- wherein determining the first target pose of the first motion arm based on the first current pose of the first motion arm and the target pose of the first end comprises:
  - selecting one of a plurality of joints of the first motion arm as a first feature joint;
  - setting a first recommended target joint value of the first feature joint; and
  - determining other target joint values of the first motion arm based on the target pose of the first end and the first recommended target joint value, or
- wherein determining the second target pose of the second motion arm based on the second current pose of the second motion arm and the target pose of the second end comprises:
  - selecting one of a plurality of joints of the second motion arm as a second feature joint;
  - setting a second recommended target joint value of the second feature joint; and
  - determining other target joint values of the second motion arm based on the target pose of the second end and the second recommended target joint value.

18. The robot system according to claim 14, wherein the target pose of the first end comprises one of the following:
- a target position and a target posture of an end arm of the first motion arm;
- a target position and a target posture of a remote center of motion (RCM) mechanism of the first motion arm; or
- a target position and a target posture of an end, for being connected to an auxiliary connection apparatus, of the first motion arm.

19. The robot system according to claim 14, wherein the target pose of the second end comprises one of the following:
- a target position and a target posture of an end arm of the second motion arm;
- a target position and a target posture of a remote center of motion (RCM) mechanism of the second motion arm; or
- a target position and a target posture of an end, for being connected to an auxiliary connection apparatus, of the second motion arm.

20. The robot system according to claim 14, wherein:
the control apparatus is further configured to:
- determine whether the other target joint values of the first motion arm are within joint motion ranges of corresponding joints; and
- increase or decrease progressively the first recommended target joint value by a predetermined adjustment value in response to determining that at least one of the other target joint values of the first motion arm is beyond the joint motion range of the corresponding joint, to adjust the first recommended target joint value, or the control apparatus is further configured to:
- determine whether the other target joint values of the second motion arm are within joint motion ranges of corresponding joints; and
- increase or decrease progressively the second recommended target joint value by a predetermined adjustment value in response to determining that at least one of the other target joint values of the second motion arm is beyond the joint motion range of the corresponding joint, to adjust the second recommended target joint value.

* * * * *